United States Patent
Faridmoayer et al.

(10) Patent No.: US 11,959,092 B2
(45) Date of Patent: Apr. 16, 2024

(54) PROCESS FOR THE MANIPULATION OF NUCLEIC ACIDS

(71) Applicant: GLAXOSMITHKLINE BIOLOGICALS SA, Rixensart (BE)

(72) Inventors: Amirreza Faridmoayer, Schlieren (CH); Michael Thomas Kowarik, Schlieren (CH); Gerd Martin Lipowsky, Schlieren (CH); Fabio Serventi, Schlieren (CH)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 799 days.

(21) Appl. No.: 16/635,352

(22) PCT Filed: Aug. 7, 2018

(86) PCT No.: PCT/EP2018/071415
§ 371 (c)(1),
(2) Date: Jan. 30, 2020

(87) PCT Pub. No.: WO2019/030234
PCT Pub. Date: Feb. 14, 2019

(65) Prior Publication Data
US 2022/0090143 A1      Mar. 24, 2022

(30) Foreign Application Priority Data
Aug. 7, 2017    (GB) ..................................... 1712678

(51) Int. Cl.
*C12N 9/00* (2006.01)
*C12N 9/10* (2006.01)
*C12N 15/90* (2006.01)

(52) U.S. Cl.
CPC ......... *C12N 15/902* (2013.01); *C12N 9/1048* (2013.01); *C12N 9/1051* (2013.01); *C12N 2800/24* (2013.01); *C12N 2800/30* (2013.01)

(58) Field of Classification Search
CPC .......................... C12N 15/902; C12N 2800/30; C12N 9/1048; C12N 9/1051; C12N 15/90; C12N 9/10; C12N 15/09; C12N 15/12; C12N 15/63; C12N 1/21; C12Y 307/01003; C07K 16/10; C12P 21/00
USPC ...................................... 536/23.2; 435/252.3
See application file for complete search history.

(56) References Cited

U.S. PATENT DOCUMENTS

2006/0094111 A1    5/2006    Saito et al.

FOREIGN PATENT DOCUMENTS

| WO | WO 01/23545 A1 | 4/2001 |
|----|----------------|--------|
| WO | 2007/011733 A2 | 1/2007 |
| WO | 2014/072405 A1 | 5/2014 |
| WO | 2014/057109 A1 | 4/2015 |
| WO | 2015/052344 A1 | 4/2015 |
| WO | 2016/020499 A2 | 2/2016 |
| WO | 2017/015545 A1 | 1/2017 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., (Structure, 2002, vol. 10: 8-9.*
Chang, Katherine et al., "Novel Heterotypic Rox Sites for Combinatorial Dre Recombination Strategies." Genes, Genomes, Genetics; 2015; pp. 559-571; vol. 6(3).
Feldman, Mario, et al, "Engineering N-linked protein glycosylation with diverse O antigen lipopolysaccharide structures in *Escherichia coli*." Proceedings of the National Academy of Sciences of The United States of America, National Academy of Sciences, US; 2005; pp. 3016-3021; vol. 102(8).
Kondo, Saki, et al. "Efficient sequential gene regulation via FLP- and Cre-recombinase using adenovirus vector in mammalian cells including mouse ES cells." Microbiol. Immunol.; 2006; pp. 831-843; vol. 50(10).
Motojima, Masaru, et al., "Conditional knockout of Foxc2 gene in kidney: efficient generation of conditional alleles of single-exon gene by double-selection system." Mammalian Genome; 2015; pp. 62-69; vol. 27(1).

(Continued)

*Primary Examiner* — Robert B Mondesi
*Assistant Examiner* — Mohammad Y Meah
(74) *Attorney, Agent, or Firm* — Birch, Stewart, Kolasch & Birch, LLP

(57) ABSTRACT

The present invention discloses a process for engineering a host cell comprising the steps of; a) integrating a first polynucleotide cassette including a first selection marker flanked by a first pair of recombination sites; b) removing the first selection marker by the action of a recombinase which recognises the first pair of recombination sites; c) integrating a second polynucleotide cassette including a second selection marker flanked by a second pair of recombination sites; and d) removing the second selection marker by the action of a recombinase which recognises the second pair of recombination sites. Also disclosed is a host cell genome polynucleotide comprising a first recombinantly engineered region and a second recombinantly engineered region, wherein a first single recombination site is adjacent to the first recombinantly engineered region, and a second single recombination site is adjacent to the second recombinantly engineered region.

4 Claims, 5 Drawing Sheets
Specification includes a Sequence Listing.

(56) References Cited

OTHER PUBLICATIONS

Shah, Riddhi, et al., "Target-specific variants of Flp recombinase mediate genome engineering reactions in mammalian cells." FEBS Journal; 2015; pp. 3323-3333; vol. 282(17).
Turan, S, et al., "Multiplexing RMCE: Versatile Extensions of the Flp-Recombinase-Mediated Cassette-Exchange Technology" Journal of Molecular Biology; 2010; pp. 52-69; vol. 402(1).
Turan, Soeren, et al., "Recombinase-mediated cassette exchange (RMCE)—A rapidly-expanding toolbox for targeted genomic modifications." Gene; 2013; pp. 1-27; vol. 515(1).

* cited by examiner ately close to each other in the genome. This problem is demonstrated in FIG. 4.

SEQUENCE LISTING

<160> NUMBER OF SEQ ID NOS: 13

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FRTwt

<400> SEQUENCE: 1
gaagttccta ttccgaagtt cctattctct agaaagtata ggaacttc                 48

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FRT3

<400> SEQUENCE: 2
gaagttccta ttccgaagtt cctattcttc aaatagtata ggaacttc                 48

<210> SEQ ID NO 3
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FRT10

<400> SEQUENCE: 3
gaagttccta ttccgaagtt cctattcact agaatgtata ggaacttc                 48

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FRT13

<400> SEQUENCE: 4
gaagttccta ttccgaagtt cctattctca tataagtata ggaacttc                 48

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: FRT14

<400> SEQUENCE: 5
gaagttccta ttccgaagtt cctattctat cagaagtata ggaacttc                48

<210> SEQ ID NO 6
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FRT15

<400> SEQUENCE: 6
gaagttccta ttccgaagtt cctattctta taggagtata ggaacttc                48

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FRT5

<400> SEQUENCE: 7
gaagttccta ttccgaagtt cctattcact agaatgtata ggaacttc                48

<210> SEQ ID NO 8
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FRT11

<400> SEQUENCE: 8
gaagttccta ttccgaagtt cctattctga actaagtata ggaacttc                48

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FRT12

<400> SEQUENCE: 9
gaagttccta ttccgaagtt cctattcttt ctgaagtata ggaacttc                48

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: FRT16

<400> SEQUENCE: 10
```
gaagttccta ttccgaagtt cctattctcc gggcagtata ggaacttc    48

<210> SEQ ID NO 11
<211> LENGTH: 423
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Recombinase

<400> SEQUENCE: 11

Met Pro Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
            20                  25                  30

Leu Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Tyr Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
225                 230                 235                 240

Pro Leu Val Tyr Leu Asp Glu Phe Leu Arg Asn Ser Glu Pro Val Leu
                245                 250                 255

Lys Arg Val Asn Arg Thr Gly Asn Ser Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Ser Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

```
Ala Val Ala Arg Thr Thr Tyr Thr His Gln Ile Thr Ala Ile Pro Asp
                340                 345                 350

His Tyr Phe Ala Leu Val Ser Arg Tyr Ala Tyr Asp Pro Ile Ser
        355                 360                 365

Lys Glu Met Ile Ala Leu Lys Asp Glu Thr Asn Pro Ile Glu Glu Trp
    370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile
                420

<210> SEQ ID NO 12
<211> LENGTH: 1269
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Recombinase

<400> SEQUENCE: 12
atgccacaat tgatatatt atgtaaaaca ccacctaagg tgcttgttcg tcagtttgtg      60
gaaaggtttg aaagaccttc aggtgagaaa atagcattat gtgctgctga actaacctat    120
ttatgttgga tgattacaca taacggaaca gcaatcaaga gagccacatt catgagctat    180
aatactatca taagcaattc gctgagtttc gatattgtca ataaatcact ccagtttaaa    240
tacaagacgc aaaaagcaac aattctggaa gcctcattaa agaaattgat tcctgcttgg    300
gaatttacaa ttattcctta ctatggacaa aaacatcaat ctgatatcac tgatattgta    360
agtagtttgc aattacagtt cgaatcatcg gaagaagcag ataagggaaa tagccacagt    420
aaaaaaatgc ttaaagcact tctaagtgag ggtgaaagca tctgggagat cactgagaaa    480
atactaaatt cgtttgagta tacttcgaga tttacaaaaa caaaaacttt ataccaattc    540
ctcttcctag ctactttcat caattgtgga agattcagcg atattaagaa cgttgatccg    600
aaatcattta aattagtcca aaataagtat ctgggagtaa taatccagtg tttagtgaca    660
gagacaaaga caagcgttag taggcacata tacttcttta gcgcaagggg taggatcgat    720
ccacttgtat atttggatga atttttgagg aattctgaac cagtcctaaa acgagtaaat    780
aggaccggca attcttcaag caataaacag gaataccaat tattaaaaga taacttagtc    840
agatcgtaca ataaagcttt gaagaaaaat gcgccttatt caatctttgc tataaaaaat    900
ggcccaaaat ctcacattgg aagacatttg atgacctcat tctttcaat gaagggccta     960 acggagttga ctaatgttgt gggaaattgg agcgataagc gtgcttctgc cgtggccagg   1020
acaacgtata ctcatcagat aacagcaata cctgatcact acttcgcact agtttctcgg   1080
tactatgcat atgatccaat atcaaaggaa atgatagcat tgaaggatga actaatcca    1140 attgaggagt ggcagcatat agaacagcta aagggtagtg ctgaaggaag catacgatac   1200
cccgcatgga atgggataat atcacaggag gtactagact acctttcatc ctacataaat   1260
agacgcata                                                           1269

<210> SEQ ID NO 13
<211> LENGTH: 9332
<212> TYPE: DNA
```

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Plasmid

<400> SEQUENCE: 13

```
gagacacaac gtggctttgt tgaataaatc gaacttttgc tgagttgaag gatcagatca      60
cgcatcttcc cgacaacgca gaccgttccg tggcaaagca aaagttcaaa atcaccaact     120
ggtccaccta caacaaagct ctcatcaacc gtggctccct cactttctgg ctggatgatg     180
gggcgattca ggcctggtat gagtcagcaa caccttcttc acgaggcaga cctcagcgcc     240
acaggtgcgg ttgctggcgc taaccgtttt tatcaggctc tgggaggcag aataaatgat     300
catatcgtca attattacct ccacggggag agcctgagca aactggcctc aggcatttga     360
gaagcacacg gtcacactgc ttccggtagt caataaaccg gtaaaccagc aatagacata     420
agcggctatt taacgaccct gccctgaacc gacgaccggg tcgaatttgc tttcgaattt     480
ctgccattca tccgcttatt atcacttatt caggcgtagc aaccaggcgt ttaagggcac     540
caataactgc cttaaaaaaa ttacgccccg ccctgccact catcgcagta ctgttgtaat     600
tcattaagca ttctgccgac atggaagcca tcacaaacgg catgatgaac ctgaatcgcc     660
agcggcatca gcaccttgtc gccttgcgta taatatttgc ccatggtgaa acgggggcg     720
aagaagttgt ccatattggc cacgtttaaa tcaaaactgg tgaaactcac ccagggattg     780
gctgagacga aaacatatt ctcaataaac cctttaggga ataggccag gttttcaccg      840
taacacgcca catcttgcga atatatgtgt agaaactgcc ggaaatcgtc gtggtattca     900
ctccagagcg atgaaaacgt ttcagtttgc tcatggaaaa cggtgtaaca agggtgaaca     960
ctatcccata tcaccagctc accgtctttc attgccatac ggaattccgg atgagcattc    1020
atcaggcggg caagaatgtg aataaaggcc ggataaaact tgtgcttatt tttctttacg    1080
gtctttaaaa aggccgtaat atccagctga acggtctggt tataggtaca ttgagcaact    1140
gactgaaatg cctcaaaatg ttctttacga tgccattggg atatatcaac ggtggtatat    1200
ccagtgattt ttttctccat tttagcttcc ttagctcctg aaaatctcga taactcaaaa    1260
aatacgcccg gtagtgatct tatttcatta tggtgaaagt tggaacctct tacgtgccga    1320
tcaacgtctc atttttcgcca aaagttggcc cagggcttcc cggtatcaac agggacacca    1380
ggatttattt attctgcgaa gtgatcttcc gtcacaggta tttattcggc gcaaagtgcg    1440
tcgggtgatg ctgccaactt actgatttag tgtatgatgg tgtttttgag gtgctccagt    1500
ggcttctgtt tctatcagct gtccctcctg ttcagctact gacggggtgg tgcgtaacgg    1560
caaaagcacc gccggacatc agcgcttgtt tcggcgtggg tatggtggca ggccccgtgg    1620
ccgggggact gttgggcgcc tgtagtgcca tttacccccca ttcactgcca gagccgtgag    1680
cgcagcgaac tgaatgtcac gaaaaagaca gcgactcagg tgcctgatgg tcggagacaa    1740
aaggaatatt cagcgatttg cccgagcttg cgagggtgct acttaagcct ttagggtttt    1800
aaggtctgtt ttgtagagga gcaaacagcg tttgcgacat ccttttgtaa tactgcggaa    1860
ctgactaaag tagtgagtta tacacagggc tgggatctat tcttttttatc ttttttttatt    1920
ctttctttat tctataaatt ataaccactt gaatataaac aaaaaaaaca cacaaaggtc    1980
tagcggaatt tacagagggt ctagcagaat ttacaagttt tccagcaaag gtctagcaga    2040
atttacagat acccacaact caaaggaaaa ggactagtaa ttatcattga ctagcccatc    2100
```

-continued

```
tcaattggta tagtgattaa atcacctag accaattgag atgtatgtct gaattagttg    2160
ttttcaaagc aaatgaacta gcgattagtc gctatgactt aacggagcat gaaaccaagc    2220
taattttatg ctgtgtggca ctactcaacc ccacgattga aaaccctaca aggaaagaac    2280
ggacggtatc gttcacttat aaccaatacg ttcagatgat gaacatcagt agggaaaatg    2340
cttatggtgt attagctaaa gcaaccagag agctgatgac gagaactgtg gaaatcagga    2400
atcctttggt taaaggcttt gagattttcc agtggacaaa ctatgccaag ttctcaagcg    2460
aaaaattaga attagttttt agtgaagaga tattgcctta tcttttccag ttaaaaaaat    2520
tcataaaata taatctggaa catgttaagt cttttgaaaa caaatactct atgaggattt    2580
atgagtggtt attaaaagaa ctaacacaaa agaaaactca caaggcaaat atagagatta    2640
gccttgatga atttaagttc atgttaatgc ttgaaaataa ctaccatgag tttaaaaggc    2700
ttaaccaatg ggttttgaaa ccaataagta aagatttaaa cacttacagc aatatgaaat    2760
tggtggttga taagcgaggc cgcccgactg atacgttgat tttccaagtt gaactagata    2820
gacaaatgga tctcgtaacc gaacttgaga caaccagat aaaaatgaat ggtgacaaaa    2880
taccaacaac cattacatca gattcctacc tacataacgg actaagaaaa acactacacg    2940
atgctttaac tgcaaaaatt cagctcacca gttttgaggc aaaattttg agtgacatgc    3000
aaagtaagta tgatctcaat ggttcgttct catggctcac gcaaaaacaa cgaaccacac    3060
tagaaacat actggctaaa tacgaagga tctgaggttc ttatggctct tgtatctatc    3120
agtgaagcat caagactaac aaacaaaagt agaacaactg ttcaccgtta catatcaaag    3180
ggaaaactgt ccatatgcac agatgaaaac ggtgtaaaaa agatagatac atcagagctt    3240
ttacgagttt ttggtgcatt taaagctgtt caccatgaac agatcgacaa tgtaacagat    3300
gaacagcatg taacacctaa tagaacaggt gaaaccagta aaacaaagca actagaacat    3360
gaaattgaac acctgagaca acttgttaca gctcaacagt cacacataga cagcctgaaa    3420
caggcgatgc tgcttatcga atcaaagctg ccgacaacac gggagccagt gacgcctccc    3480
gtggggaaaa aatcatggca attctggaag aaatagcgcc tgtttcgttt caggcaggtt    3540
atcagggagt gtcagcgtcc tgcggttctc cggggcgttc gggtcatgca gcccgtaatg    3600
gtgatttacc agcgtctgcc aggcatcaat tctaggcctg tctgcgcggt cgtagtacgg    3660
ctggaggcgt tttccggtct gtagctccat gttcggaatg acaaaattca gctcaagccg    3720
tcccttgtcc tggtgctcca cccacaggat gctgtactga tttttttcga gaccgggcat    3780
cagtacacgc tcaaagctcg ccatcacttt ttcacgtcct cccggcggca gctccttctc    3840
cgcgaacgac agaacaccgg acgtgtattt cttcgcaaat ggcgtggcat cgatgagttc    3900
ccggacttct tccggattac cctgaagcac cgttgcgcct tcgcggttac gctccctccc    3960
cagcaggtaa tcaaccggac cactgccacc accttttccc ctggcatgaa atttaactat    4020
catcccgcgc cccctgttcc ctgacagcca gacgcagccg gcgcagctca tccccgatgg    4080
ccatcagtgc ggccaccacc tgaacccggt caccggaaga ccactgcccg ctgttcacct    4140
tacgggctgt ctgattcagg ttatttccga tggcggccag ctgacgcagt aacggcggtg    4200
ccagtgtcgg cagttttccg gaacgggcaa ccggctcccc caggcagacc cgccgcatcc    4260
ataccgccag ttgtttaccc tcacagcgtt caagtaaccg gcatgttca tcatcagtaa    4320
cccgtattgt gagcatcctc tcgcgtttca tcggtatcat taccccatga acagaaatcc    4380
cccttacacg gaggcatcag tgactaaacg gggtctgacg ctcagtggaa cgaaaactca    4440
cgttaaggga ttttggtcat gagattatca aaaaggatct tcacctagat ccttttaaat    4500
```

```
taaaaatgaa gttttaaatc aatctaaagt atatatgagt aaacttggtc tgacagttac    4560
caatgcttaa tcagtgaggc acctatctca gcgatctgtc tatttcgttc atccatagtt    4620
gcctgactcc ccgtcgtgta gataactacg atacgggagg gcttaccatc tggccccagt    4680
gctgcaatga taccgcgaga cccacgctca ccggctccag atttatcagc aataaaccag    4740
ccagccggaa gggccgagcg cagaagtggt cctgcaactt tatccgcctc catccagtct    4800
attaattgtt gccgggaagc tagagtaagt agttcgccag ttaatagttt gcgcaacgtt    4860
gttgccattg ctgcaggcat cgtggtgtca cgctcgtcgt ttggtatggc ttcattcagc    4920
tccggttccc aacgatcaag gcgagttaca tgatcccca tgttgtgcaa aaaagcggtt    4980
agctccttcg gtcctccgat cgttgtcaga agtaagttgg ccgcagtgtt atcactcatg    5040
gttatggcag cactgcataa ttctcttact gtcatgccat ccgtaagatg cttttctgtg    5100
actggtgagt actcaaccaa gtcattctga gaatagtgta tgcggcgacc gagttgctct    5160
tgcccggcgt caacacggga taataccgcg ccacatagca gaactttaaa agtgctcatc    5220
attggaaaac gttcttcggg gcgaaaactc tcaaggatct taccgctgtt gagatccagt    5280
tcgatgtaac ccactcgtgc acccaactga tcttcagcat cttttacttt caccagcgtt    5340
tctgggtgag caaaaacagg aaggcaaaat gccgcaaaaa agggaataag ggcgacacgg    5400
aaatgttgaa tactcatact cttccttttt caatattatt gaagcattta tcagggttat    5460
tgtctcatga gcggatacat atttgaatgt atttagaaaa ataaacaaat aggggttccg    5520
cgcacatttc cccgaaaagt gccacctgac gtctaagaaa ccattattat catgacatta    5580
acctataaaa ataggcgtat cacgaggccc tttcgtcttc aagaattta taaaccgtgg    5640 agcgggcaat actgagctga tgagcaattt ccgttgcacc agtgcccttc tgatgaagcg    5700
tcagcacgac gttcctgtcc acggtacgcc tgcggccaaa tttgattcct ttcagctttg    5760
cttcctgtcg gccctcattc gtgcgctcta ggatcctcta cgccggacgc atcgtggccg    5820
gcatcaccgg cgctgaggtc tgcctcgtga agaaggtgtt gctgactcat accaggcctg    5880
aatcgcccca tcatccagcc agaaagtgag ggagccacgg ttgatgagag ctttgttgta    5940
ggtggaccag ttggtgattt tgaactttg ctttgccacg gaacggtctg cgttgtcggg    6000
aagatgcgtg atctgatcct tcaactcagc aaaagttcga tttattcaac aaagccgccg    6060
tcccgtcaag tcagcgtaat gctctgccag tgttacaacc aattaaccaa ttctgattag    6120
aaaaactcat cgagcatcaa atgaaactgc aatttattca tatcaggatt atcaatacca    6180 tattttgaa aaagccgttt ctgtaatgaa ggagaaaact caccgaggca gttccatagg    6240
atggcaagat cctggtatcg gtctgcgatt ccgactcgtc aacatcaat acaacctatt    6300 aatttcccct cgtcaaaaat aaggttatca agtgagaaat caccatgagt gacgactgaa    6360
tccggtgaga atggcagaat aggaacttcg gaataggaac ttcaaagcgt ttccgaaaac    6420
gagcgcttcc gaaaatgcaa cgcgagctgc gcacatacag ctcactgttc acgtcgcacc    6480
tatatctgcg tgttgcctgt atatatatat acatgagaag aacggcatag tgcgtgttta    6540
tgcttaaatg cgtacttata tgcgtctatt tatgtaggat gaaaggtagt ctagtacctc    6600
ctgtgatatt atcccattcc atgcggggta tcgtatgctt ccttcagcac tacccttag    6660 ctgttctata tgctgccact cctcaattgg attagtctca tccttcaatg ctatcatttc    6720
ctttgatatt ggatcatatg catagtaccg agaaactagt gcgaagtagt gatcaggtat    6780
tgctgttatc tgatgagtat acgttgtcct ggccacggca gaagcacgct tatcgctcca    6840
```

```
atttcccaca acattagtca actccgttag gcccttcatt gaaagaaatg aggtcatcaa    6900
atgtcttcca atgtgagatt ttgggccatt ttttatagca aagattgaat aaggcgcatt    6960
tttcttcaaa gctttattgt acgatctgac taagttatct tttaataatt ggtattcctg    7020
tttattgctt gaagaattgc cggtcctatt tactcgtttt aggactggtt cagaattcct    7080
caaaaattca tccaaatata caagtggatc gatcctaccc cttgcgctaa agaagtatat    7140
gtgcctacta acgcttgtct ttgtctctgt cactaaacac tggattatta ctcccagata    7200
cttattttgg actaatttaa atgatttcgg atcaacgttc ttaatatcgc tgaatcttcc    7260
acaattgatg aaagtagcta ggaagaggaa ttggtataaa gttttgttt ttgtaaatct     7320
cgaagtatac tcaaacgaat ttagtatttt ctcagtgatc tcccagatgc tttcacccctc   7380
acttagaagt gctttaagca tttttttact gtggctattt cccttatctg cttcttccga    7440
tgattcgaac tgtaattgca aactacttac aatatcagtg atatcagatt gatgttttg     7500
tccatagtaa ggaataattg taaattccca agcaggaatc aatttcttta atgaggcttc    7560
cagaattgtt gcttttgcg tcttgtattt aaactggagt gatttattga caatatcgaa     7620
actcagcgaa ttgcttatga tagtattata gctcatgaat gtggctctct tgattgctgt    7680
tccgttatgt gtaatcatcc aacataaata ggttagttca gcagcacata atgctatttt    7740
ctcacctgaa ggtctttcaa acctttccac aaactgacga caagcacct taggtggtgt     7800
tttacataat atatcaaatt gtggcataca acctccttag tacatgcaac cattatcacc    7860
gccagaggta aaatagtcaa cacgcacggt gttagatatt tatcccttgc ggtgatagat    7920
ttaacgtatg agcacaaaaa agaaaccatt aacacaagag cagcttgagg acgcacgtcg    7980
ccttaaagca atttatgaaa aaagaaaaa tgaacttggc ttatcccagg aatctgtcgc     8040
agacaagatg gggatggggc agtcaggcgt tggtgcttta tttaatggca tcaatgcatt    8100
aaatgcttat aacgccgcat tgcttacaaa aattctcaaa gttagcgttg aagaatttag    8160
cccttcaatc gccagagaaa tctacgagat gtatgaagcg gttagtatgc agccgtcact    8220
tagaagtgag tatgagtacc ctgttttttc tcatgttcag gcagggatgt tctcacctaa    8280
gcttagaacc tttaccaaag gtgatgcgga gagatgggta agcacaacca aaaaagccag    8340
tgattctgca ttctggcttg aggttgaagg taattccatg accgcaccaa caggctccaa    8400
gccaagcttt cctgacggaa tgttaattct cgttgaccct gagcaggctg ttgagccagg    8460
tgatttctgc atagccagac ttgggggtga tgagtttacc ttcaagaaac tgatcaggga    8520
tagcggtcag gtgttttac aaccactaaa cccacagtac ccaatgatcc catgcaatga     8580
gagttgttcc gttgtgggga aagttatcgc tagtcagtgg cctgaagaga cgtttggctg    8640
atcggcaagg tgttctggtc ggcgcatagc tgataacaat tgagcaagaa tctgcatttc    8700
tttccagact tgttcaacag gccagccatt acgctcgtca tcaaaatcac tcgcatcaac    8760
caaaccgtta ttcattcgtg attgcgcctg agcgagacga aatacgcgat cgctgttaaa    8820
aggacaatta caaacaggaa tcgaatgcaa ccggcgcagg aacactgcca gcgcatcaac    8880
aatattttca cctgaatcag gatattcttc taatacctgg aatgctgttt tcccggggat    8940
cgcagtggta agtaaccatg catcatcagg agtacggata aaatgcttga tggtcggaag    9000
aggcataaat tccgtcagcc agtttagtct gaccatctca tctgtaacat cattggcaac    9060
```

-continued

```
gctacctttg ccatgtttca gaaacaactc tggcgcatcg ggcttcccat acaatcgata    9120
gattgtcgca cctgattgcc cgacattatc gcgagcccat ttatacccat ataaatcagc    9180
atccatgttg gaatttaatc gcggcctcga gcaagacgtt tcccgttgaa tatggctcat    9240
aacacccctt gtattactgt ttatgtaagc agacagtttt attgttcatg atgatatatt    9300
tttatcttgt gcaatgtaac atcagagatt tt                                  9332
```

PROCESS FOR THE MANIPULATION OF NUCLEIC ACIDS

CROSS-REFERENCE TO RELATED APPLICATIONS

This application is filed pursuant to 35 U.S.C. § 371 as a United States National Phase Application of International Application No. PCT/EP2018/071415 filed Aug. 7, 2018 which claims priority from GB 1712678.0 filed Aug. 7, 2017.

SEQUENCE LISTING

The instant application contains a Sequence Listing which has been submitted electronically in ASCII format and is hereby incorporated by reference in its entirety. Said ASCII copy, created on Nov. 6, 2020, is named VB66338_US_SEQLST.txt and is 20,914 bytes in size.

TECHNICAL FIELD

The present invention relates to the field of recombinant manipulation of nucleic acids and specifically to the precise removal of specific regions of nucleic acid whilst ensuring that required portions of nucleic acid are not removed. Specifically, the present invention allows the removal of multiple unwanted genetic elements which may have been incorporated, for example as selection markers, during recombinant manipulation of a genomic polynucleotide. The process uses short recombination sites, such as FRT sites, to flank a genetic element which is to be subsequently removed. The use of non-identical recombination sites to flank different genetic elements which are to be removed allows efficient removal of the intended genetic elements without loss of other elements from the genomic polynucleotide.

BACKGROUND

The genetic manipulation of prokaryotic and eukaryotic organisms often involves the stable insertion of genetic elements into the genome so that a stable line with the required attribute can be generated. Alternatively, genetic manipulation may be used to remove unwanted elements of genetic material, optionally replacing the removed genetic material with other genetic inserts. Selection markers are usually introduced during the genetic manipulation so that cells containing the correct genetic manipulation can be selected. However, it is useful to subsequently remove the markers once a correctly manipulated host cell has been established, especially if the host cell is to be used for the manufacture of products for medical or veterinary use.

The removal of single genetic markers from a genome is known. The Flp recombinase was discovered to have a role in the inversion of yeast genetic material (Broach and Hicks (1980) Cell 21; 501-506, Broach et al (1982) Cell 29; 227-234). The potential of the Flp recombinase was investigated in E. coli (Cox (1983) P.N.A.S. 80; 4223-4227, Vetter et al (1983) PNAS 80; 7204-7288, Andrews et al (1985) Cell 40; 795-803) and roles for Flp-recombinase in excision, inversion, translocation and insertion of genetic elements were elucidated (Gronostajski and Sadowski (1985) J. Biol. Chem. 260; 12328-35). The Flp-recombinase produces recombination between Flp recombinase target (FRT) sites which are genetic elements of about 48 bp. FRT sites have been used to flank a selection marker, enabling its subsequent excision from a yeast genome using Flp recombinase (Cregg and Madden (1989) Mol. Gen. Genet. 219; 320-323) and a similar strategy has been used to excise antibiotic resistance markers in E. coli (Cherepanov and Wackernagel (1995) Gene 158; 9-14).

More complex genetic manipulation of prokaryotic and eukaryotic organisms requires the stable integration and/or removal of multiple genetic elements into/from the genome. For example, the manipulation of E. coli to produce proteins linked to specific saccharides has been described (WO 09/104074, WO 11/60615, WO 11/138361). In order to accomplish the production of bioconjugates in E. coli, it is necessary to introduce multiple genetic elements into the host cell, including one or more copies of several genes encoding the glycotransferases which are needed to assemble the required saccharide chain, a gene encoding an oligosaccharyltransferase such as PglB, a gene encoding the required protein containing a glycosylation site and potentially further genes encoding other enzymes such as polymerases, co-polymerases, flippases and/or enzymes to correctly decorate the saccharide. It is also beneficial to remove specific genetic elements such as lipopolysaccharide 0-antigen ligase, native glycosyltransferase or oligosaccharyl transferase, flippases, polymerases or co-polymerases. It would be beneficial to integrate several of these genes into the production cell genome and to remove unwanted genes, in order to facilitate production (WO 14/57109, WO 15/52344). However, this is difficult using the standard methods (Datsenko and Wanner (2000) PNAS 97; 6640-5, Kuhlman and Cox (2010) 38; e92). In particular, it is difficult to remove the multiple selection markers associated with multiple integrations since interference can occur between the recombination sites flanking the selection markers resulting in the excision of some of the required genetic material as well as selection markers. This is particular problematic if the selection markers to be excised are positioned relatively close to each other in the genome. This problem is demonstrated in FIG. 4.

The present invention provides a solution to this problem by using pairs of identical recombination sites to flank each nucleic acid segment to be removed from the genome; wherein each identical pair of recombination sites is different to the pair of recombination sites flanking other nucleic acid segments to be removed from the genome.

Accordingly, there is provided a method of removing at least two portions of insert nucleic acid from a genomic polynucleotide in a host cell, said method comprising the steps of:

a) preparing a genomic polynucleotide comprising a first insert nucleic acid which is flanked by a pair of first recombination sites in the same orientation which are identical to each other and have a first nucleic acid sequence;

b) exposing the genomic polynucleotide of step a) to a recombinase that recognises the first recombination sites such that the identical recombination sites recombine resulting in the excision of the first insert nucleic acid and one of the first recombination sites;

c) inserting into the genomic polynucleotide of step b) a second insert nucleic acid flanked by a pair of second recombination sites in the same orientation wherein the second recombination sites are identical to each other and have a second nucleic acid sequence which shares no more than 98% sequence identity with the first nucleic acid sequence; and d) Exposing the genomic polynucleotide of step c) to a recombinase that recognises the second recombination sites such that the identical recombination sites recombine resulting in the excision of the second insert nucleic acid and one of the second recombination sites but without the removal of genomic polynucleotide sequence which is not flanked by identical recombination sites.

Accordingly, there is also provided a method for removing at least two portions of insert nucleic acid from a genomic polynucleotide in a host cell, said method comprising the steps of:
  a) preparing a genomic polynucleotide comprising at least a first and a second insert nucleic acids, wherein i) the first insert nucleic acid is flanked by first recombination sites in the same orientation which are identical to each other and have a first nucleic acid sequence ii) the second insert nucleic acid is flanked by second recombination sites in the same orientation which are identical to each other and have a second nucleic acid sequence which shares no more than 98% sequence identity with the first nucleic acid sequence and iii) any further recombination sites have a nucleic acid sequence that shares no more than 98% sequence identity with the first or second nucleic acid sequences; and
  b) exposing the genomic polynucleotide to a recombinase that recognises the first and second recombination sites such that the identical recombination sites recombine resulting in the excision of the insert nucleic acid flanked by identical recombination sites but without the removal of genomic polynucleotide which is not flanked by identical recombination sites.

Without wishing to be bound by theory, the use of non-identical pairs of recombination sites favours recombination between the identical pairs of recombination sites so that the expected nucleic acid segments are preferentially removed.

In a second aspect of the invention, there is provided a host cell comprising a genomic polynucleotide prepared by the method of the invention.

In a third aspect of the invention, there is provided a host cell genome polynucleotide comprising a first recombinantly engineered region and a second recombinantly engineered region, wherein a first single recombination site is adjacent to the first recombinantly engineered region, and a second single recombination site is adjacent to the second recombinantly engineered region, wherein the first and second recombination sites have nucleotide sequences which share 90-98% identity with each other and with the nucleic acid sequence of any further recombination sites present in the host cell genome polynucleotide.

In a fourth aspect of the invention, there is provided a host cell comprising a host cell genome polynucleotide containing a first recombinantly engineered region and a second recombinantly engineered region, wherein a first recombination site scar is adjacent to the first recombinantly engineered region and a second recombination site scar is adjacent to the second recombinantly engineered region; wherein the first and second recombination site scars have a different polynucleotide sequences which are less than 98% identical to each other and less than 98% identical to the polynucleotide sequence of any further recombination site scar present in the host cell genome polynucleotide.

In a fifth aspect of the invention, there is provided a process for making a glycosylated protein comprising the steps of;

a) Culturing the host cell of the invention under conditions suitable for the production of glycosylated protein and
  b) Isolating the glycosylated protein from the culture.

In a sixth aspect of the invention, there is provided a prokaryotic genomic polynucleotide or a eukaryotic chromosome comprising at least two recombination site scars adjacent to at least two recombination regions, wherein each recombination site scar has a different polynucleotide sequence.

In a seventh aspect of the invention, there is provided a process for engineering a host cell comprising the steps of;
  a) integrating a first polynucleotide cassette including a first selection marker flanked by a first pair of recombination sites;
  b) removing the first selection marker by the action of a recombinase which recognises the first pair of recombination sites;
  c) integrating a second polynucleotide cassette including a second selection marker flanked by a second pair of recombination sites; and
  d) removing the second selection marker by the action of a recombinase which recognises the second pair of recombination sites;
  wherein the first pair of recombination sites have an identical nucleic acid sequence and the second pair of recombination sites have an identical nucleic acid sequence and the first and second pairs of recombination sites share 90-98% nucleic acid sequence identity.

In an eighth aspect of the invention, there is provided an engineered host cell obtainable by the process of the invention. For example, an engineered host cell is optionally modified by inserting multiple copies of a particular gene or gene cluster. A particular loci for integration can be selected to optimize the level of expression of different genes. Similarly, the integration of 2, 3, 4, 5, 6 or more copies of a gene or gene cluster at different loci can optimize the expression of the gene or gene cluster.

DETAILED DESCRIPTION

Figure 1:
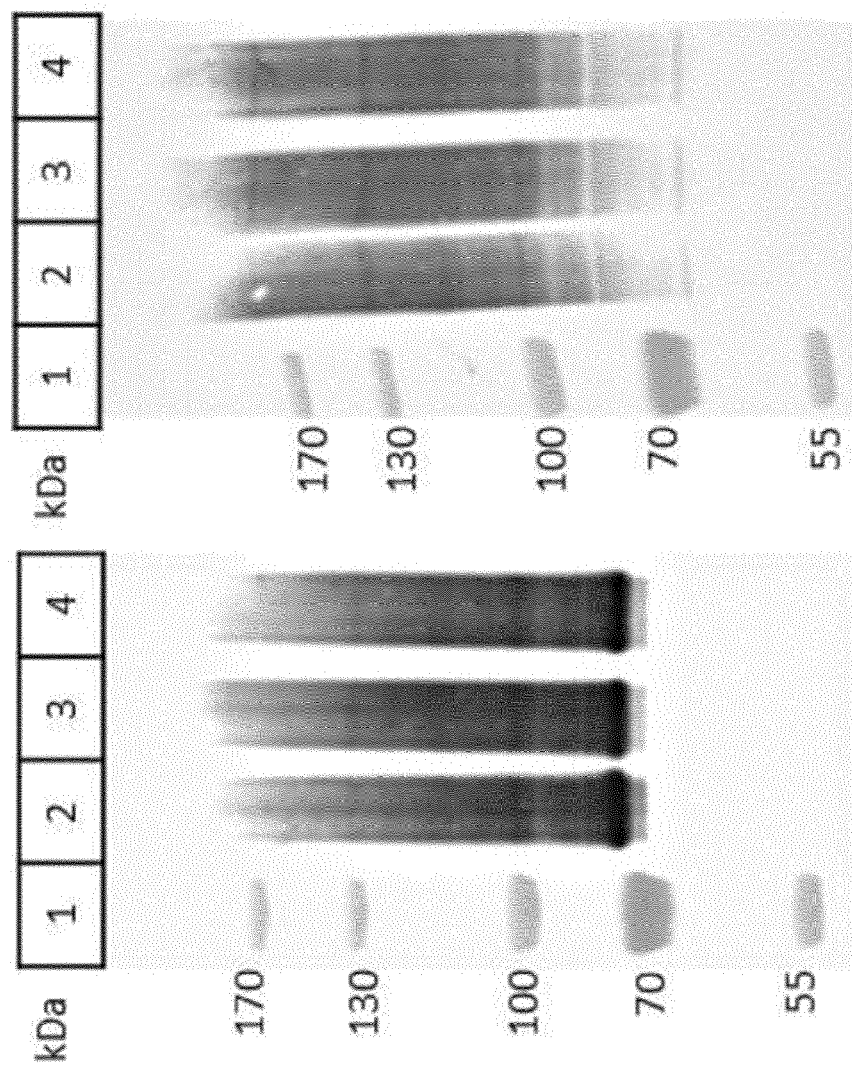
FIG. 1—Western blot on SDS PAGE loaded with periplasmic extracts. Left panel: detection with His antiserum. Right panel: detection with anti 33F antiserum. Lane 1 contains molecular weight markers, lane 2 contains strain 8661, lane 3 contains strain 10852 and lane 4 contains strain 10853.

The invention provides a method of removing at least two portions of insert nucleic acid from a genomic polynucleotide in a host cell, said method comprising the steps of:
a) preparing a genomic polynucleotide comprising a first insert nucleic acid which is flanked by a pair of first recombination sites in the same orientation which are identical to each other and have a first nucleic acid sequence;
b) exposing the genomic polynucleotide of step a) to a recombinase that recognises the first recombination sites such that the identical recombination sites recombine resulting in the excision of the first insert nucleic acid and one of the first recombination sites;
c) inserting into the genomic polynucleotide of step b) a second insert nucleic acid flanked by a pair of second recombination sites in the same orientation wherein the second recombination sites are identical to each other and have a second nucleic acid sequence which shares no more than 98% sequence identity with the first nucleic acid sequence; and
d) exposing the genomic polynucleotide of step c) to a recombinase that recognises the second recombination sites such that the identical recombination sites recombine resulting in the excision of the second insert nucleic acid and one of the second recombination sites but without the removal of genomic polynucleotide sequence which is not flanked by identical recombination sites.

The invention also provides a method for removing at least two portions of insert nucleic acid from a genomic polynucleotide in a host cell, said method comprising the steps of:
a) preparing a genomic polynucleotide comprising at least a first and a second insert nucleic acids, wherein i) the first insert nucleic acid is flanked by a pair of first recombination sites in the same orientation which are identical to each other and have a first nucleic acid sequence ii) the second insert nucleic acid is flanked by a second pair of second recombination sites in the same orientation which are identical to each other and have a second nucleic acid sequence which shares no more than 98% sequence identity with the first nucleic acid sequence and iii) any further recombination sites have a nucleic acid sequence that shares no more than 98% sequence identity with the first or second nucleic acid sequences; and
b) exposing the genomic polynucleotide to a recombinase that recognises the first and second recombination sites such that the identical recombination sites recombine resulting in the excision of the insert nucleic acid flanked by identical recombination sites but without the removal of genomic polynucleotide which is not flanked by identical recombination sites.

Whilst not wishing to be bound by theory, the use of non-identical pairs of recombination sites favours recombination between the identical pairs of recombination sites so that the expected sections of nucleic acid are preferentially removed.

The term "insert nucleic acid" means a nucleic acid segment which becomes integrated into a genomic polynucleotide as a result of a genetic manipulation of the genomic polynucleotide. The insert nucleic acid is typically a nucleic acid segment which become integrated into the genomic polynucleotide as an unwanted consequence of the genetic recombination process rather a nucleic acid segment, for example a gene to be expressed, which it is the aim of the genetic recombination to introduce. Thus the insert nucleic acid is optionally a genetic marker such as an antibiotic resistance marker. Alternatively the insert nucleic acid is a sequence inserted into the genomic polynucleotide to aid homologous recombination, for example a "landing pad". The purpose of the present invention is to provide an efficient way of removing insert nucleic acid from the genomic polynucleotide effectively once the required multiple genetic manipulations have been completed.

The term "recombination sites" means sequences on either side of insert nucleic acid which allow its subsequent removal from the genomic polynucleotide by genetic recombination mediated by a recombinase. These are typically nucleotide sequences recognised by a recombinase, allowing deletion of the intervening sequence following homologous recombination.

The term "recombinantly engineered region" means a part of the genomic polynucleotide that has been engineered. This could involve to addition of nucleic acid sequence, the deletion of nucleic acid sequence or the replacement of nucleic acid sequence.

The term "genomic polynucleotide" means a large piece of genetic material, for example a eukaryotic chromosome or prokaryotic genetic material.

The term "host cell" means a prokaryotic or eukaryotic cell. Typically, the host cell has been genetically manipulated to contain new genetic material and/or to remove genetic material. In an embodiment, multiple genetic manipulations will have been carried out on the host cell, resulting in at least 2, 3, 4, 5, 6 7, 8, 9 or 10 insert nucleic acids which can be efficiently excised using the method of the invention.

The method of the invention may be used to remove insert nucleic acid following any form of previous genetic manipulation. For example, the insert nucleic acid may be present in the genomic polynucleotide as the results of addition of genetic material, removal of genetic material or replacement of deleted genetic material with additional genetic material. The method of the invention is suitable for use with prokaryotic genomic polynucleotides, with plasmids or with eukaryotic chromosomes.

In an embodiment, the first and second insert nucleic acids are selection markers, for example, selection markers used to identify host cells in which host cell the addition, removal or replacement of genetic material has successfully occurred. In an embodiment, the selection markers are antibiotic resistance markers. In an embodiment the selection markers encode proteins that confer resistance to and antibiotic, for example ampicillin, kanamycin, chloramphenicol, spectinomycin or gentamycin.

In an embodiment, the pair of recombination sites flanking the insert nucleic acid are identical to each other. In an embodiment, the pairs of recombination sites flanking an insert nucleic acid are in the same orientation. This allows efficient recombination to occur in the presence of a recombinase that recognised the recombination site, resulting in the deletion of the insert nucleic acid and one of the recombination sites. Such recombination results in a single recombination site remaining; i.e. as a "recombination site scar" in the genomic polynucleotide.

In an embodiment, the first and second pair of recombination sites have nucleic acid sequences which share no more than 98%, 96%, 94%, 92%, 90%, 85%, 80%, 75% or 70% identity. In an embodiment, the first and second pair of recombination sites have nucleic acid sequences which share 70-98%, 75-98%, 80-98%, 85-98%, 90-98%, 92-98%, 94-98% or 96-98% identity. In a suitable embodiment, the first and second pairs of recombination sites share 90-98% identity between the sequence of the first recombination site and the sequence of the second recombination site.

In an embodiment the first and second recognition sites share no more than 98%, 96%, 94%, 92%, 90%, 85%, 80%, 75% or 70% identity to any other recombination site in the genomic polynucleotide. In an embodiment, the first and second recombination sites have nucleic acid sequences which share 70-98%, 75-98%, 80-98%, 85-98%, 90-98%, 92-98%, 94-98% or 96-98% identity with any other recombination site present in the genomic polynucleotide. In a suitable embodiment, the first and second pairs of recombination sites share 90-98% identity between the sequence of the first recombination site and the sequence of the second recombination site and any further recombination site present in the genomic polynucleotide.

In an embodiment, step a) prepares a genomic polynucleotide comprising a third insert nucleic acid which is flanked by a set of identical third recombination sites having a third nucleic acid sequence which shares no more than 98% 96%, 94%, 92% or 90% or 50%-98%, 60%-98%, 70%-98%, 80%-98%, 85%-98% 90-98%, 92-98%, 94%-98%, or 96%-98% sequence identity with the nucleic acid sequence of the first or second recombination site or any further recombination sites. In a suitable embodiment the third recombination site shares 90-98% identity with the first or second recombination site or any further recombination sites.

In an embodiment, step a) prepares a genomic polynucleotide comprising a fourth insert nucleic acid which is flanked by a set of identical fourth recombination sites having a fourth nucleic acid sequence which shares no more than 98%, 96%, 94%, 92% or 90% or 50%-98%, 60%-98%, 70%-98%, 80%-98%, 85%-98% 90-98%, 92-98%, 94%-98%, or 96%-98% sequence identity with the first nucleic acid sequence, second nucleic acid sequence, third nucleic acid sequence or the nucleic acid sequence of any further recombination sites. In a suitable embodiment the fourth recombination site shares 90-98% identity with the first or second recombination site or any further recombination sites.

In an embodiment, step a) prepares a genomic polynucleotide comprising a fifth insert nucleic acid which is flanked by a set of identical fifth recombination sites having a fifth nucleic acid sequence which shares no more than 98% 96%, 94%, 92% or 90% or 50%-98%, 60%-98%, 70%-98%, 80%-98%, 85%-98% 90-98%, 92-98%, 94%-98%, or 96%-98% sequence identity with the first nucleic acid sequence, second nucleic acid sequence, third nucleic acid sequence, fourth nucleic acid or the nucleic acid sequence of any further recombination sites. In a suitable embodiment the fifth recombination site shares 90-98% identity with the first or second recombination site or any further recombination sites In an embodiment, step a) prepares a genomic polynucleotide comprising a sixth insert nucleic acid which is flanked by a set of identical sixth recombination sites having a sixth nucleic acid sequence which shares no more than 98% 96%, 94%, 92% or 90% or 50%-98%, 60%-98%, 70%-98%, 80%-98%, 85%-98% 90-98%, 92-98%, 94%-98%, or 96%-98% sequence identity with the first nucleic acid sequence, second nucleic acid sequence, third nucleic acid sequence, fourth nucleic acid, fifth nucleic acid or the nucleic acid sequence of any further recombination sites. In a suitable embodiment the sixth recombination site shares 90-98% identity with the first or second recombination site or any further recombination sites.

The principles for the design of FRT sites is described in Turan S, Kuehle J, Schambach A, Baum C and Bode J (2010) J. Mol. Biol. 402; 52-69. For example, a typical FRT site consists of 48 base pairs consisting of two inverted 13-bp repeats (a' and a) around a 8-bp spacer and a further repeat (b), separated by a 1-bp gap in the direct orientation to the adjacent repeat:

b------→a'-----→spacer←---a

Variation is typically introduced into the spacer sequence. Preferably, the AT content of the spacer is above 75%. Preferably alterations are made to the bp at at least one of positions 2, 3, 4, 5, 6 or 7 of the spacer. Preferably positions 1 and 8 of the spacer are unchanged. Preferably no major interruptions of the 5'-polypyrimidine tracts is made.

In an embodiment, the genomic polynucleotide prepared in step a) comprises 2, 3, 4, 5, 6, 7, 8, 9, or 10 insert nucleic acids each flanked with identical pairs of recombination sites wherein each pair of recombination sites are different to other pairs of recombination sites for example, a particular pairs of recombination sites shares 90%-98% sequence identity with any other pair of recombination sites in the genomic polynucleotide.

In an embodiment, the recombination sites are 30-50, or 40-50 base pairs in length, preferably 48 base pairs in length. In an embodiment, the recombination sites are recognised by a recombinase. In an embodiment, the recombinase is preferably a FLP-recombinase. For example, the first and second recombination sites (as pairs or post-recombination, as scars) are different to each other flippase recognition target (FRT) sites or variant FRT sites.

In an embodiment the first recombination site is a FRT site having the sequence 5'-gaagttcctattccgaagttcctat-tctctagaaagtataggaacttc-3' (SEQ ID NO:1) and the second recombination site is a FRT site having the sequence of SEQ ID NO:2.

In an embodiment the first recombination site is a FRT site having the sequence 5'-gaagttcctattccgaagttcctat-tctctagaaagtataggaacttc-3' (SEQ ID NO:1) and the second recombination site is a FRT site having the sequence of SEQ ID NO:3.

In an embodiment the first recombination site is a FRT site having the sequence 5'-gaagttcctattccgaagttcctat-tctctagaaagtataggaacttc-3' (SEQ ID NO:1) and the second recombination site is a FRT site having the sequence of SEQ ID NO:4.

In an embodiment the first recombination site is a FRT site having the sequence 5'-gaagttcctattccgaagttcctat-tctctagaaagtataggaacttc-3' (SEQ ID NO:1) and the second recombination site is a FRT site having the sequence of SEQ ID NO:5.

In an embodiment the first recombination site is a FRT site having the sequence 5'-gaagttcctattccgaagttcctat-tctctagaaagtataggaacttc-3' (SEQ ID NO:1) and the second recombination site is a FRT site having the sequence of SEQ ID NO:6.

In an embodiment the first recombination site is a FRT site having the sequence 5'-gaagttcctattccgaagttcctat-tctctagaaagtataggaacttc-3' (SEQ ID NO:1) and the second recombination site is a FRT site having the sequence of SEQ ID NO:7.

In an embodiment the first recombination site is a FRT site having the sequence 5'-gaagttcctattccgaagttcctattctctagaaagtataggaacttc-3' (SEQ ID NO:1) and the second recombination site is a FRT site having the sequence of SEQ ID NO:8.

In an embodiment the first recombination site is a FRT site having the sequence 5'-gaagttcctattccgaagttcctat-tctctagaaagtataggaacttc-3' (SEQ ID NO:1) and the second recombination site is a FRT site having the sequence of SEQ ID NO:9.

In an embodiment the first recombination site is a FRT site having the sequence 5'-gaagttcctattccgaagttcctat-tctctagaaagtataggaacttc-3' (SEQ ID NO:1) and the second recombination site is a FRT site having the sequence of SEQ ID NO:10.

In an embodiment the first recombination site is a FRT site having the sequence of SEQ ID NO:2 and the second recombination site is a FRT site having the sequence of SEQ ID NO:3.

In an embodiment the first recombination site is a FRT site having the sequence of SEQ ID NO:2 and the second recombination site is a FRT site having the sequence of SEQ ID NO:4.

In an embodiment the first recombination site is a FRT site having the sequence of SEQ ID NO:2 and the second recombination site is a FRT site having the sequence of SEQ ID NO:5.

In an embodiment the first recombination site is a FRT site having the sequence of SEQ ID NO:2 and the second recombination site is a FRT site having the sequence of SEQ ID NO:6.

In an embodiment the first recombination site is a FRT site having the sequence of SEQ ID NO:2 and the second recombination site is a FRT site having the sequence of SEQ ID NO:7.

In an embodiment the first recombination site is a FRT site having the sequence of SEQ ID NO:2 and the second recombination site is a FRT site having the sequence of SEQ ID NO:8.

In an embodiment the first recombination site is a FRT site having the sequence of SEQ ID NO:2 and the second recombination site is a FRT site having the sequence of SEQ ID NO:9.

In an embodiment the first recombination site is a FRT site having the sequence of SEQ ID NO:2 and the second recombination site is a FRT site having the sequence of SEQ ID NO:10.

In an embodiment the first recombination site is a FRT site having the sequence of SEQ ID NO:2 and the second recombination site is a FRT site having the sequence of SEQ ID NO:1.

In an embodiment the first recombination site is a FRT site having the sequence of SEQ ID NO:3 and the second recombination site is a FRT site having the sequence of SEQ ID NO:4.

In an embodiment the first recombination site is a FRT site having the sequence of SEQ ID NO:3 and the second recombination site is a FRT site having the sequence of SEQ ID NO:5.

In an embodiment the first recombination site is a FRT site having the sequence of SEQ ID NO:3 and the second recombination site is a FRT site having the sequence of SEQ ID NO:6.

In an embodiment the first recombination site is a FRT site having the sequence of SEQ ID NO:3 and the second recombination site is a FRT site having the sequence of SEQ ID NO:7.

In an embodiment the first recombination site is a FRT site having the sequence of SEQ ID NO:3 and the second recombination site is a FRT site having the sequence of SEQ ID NO:8.

In an embodiment the first recombination site is a FRT site having the sequence of SEQ ID NO:3 and the second recombination site is a FRT site having the sequence of SEQ ID NO:9.

In an embodiment the first recombination site is a FRT site having the sequence of SEQ ID NO:3 and the second recombination site is a FRT site having the sequence of SEQ ID NO:10.

In an embodiment the first recombination site is a FRT site having the sequence of SEQ ID NO:3 and the second recombination site is a FRT site having the sequence of SEQ ID NO:1.

In an embodiment the first recombination site is a FRT site having the sequence of SEQ ID NO:3 and the second recombination site is a FRT site having the sequence of SEQ ID NO:2.

In an embodiment the first recombination site is a FRT site having the sequence of SEQ ID NO:4 and the second recombination site is a FRT site having the sequence of SEQ ID NO:5.

In an embodiment the first recombination site is a FRT site having the sequence of SEQ ID NO:4 and the second recombination site is a FRT site having the sequence of SEQ ID NO:6.

In an embodiment the first recombination site is a FRT site having the sequence of SEQ ID NO:4 and the second recombination site is a FRT site having the sequence of SEQ ID NO:7.

In an embodiment the first recombination site is a FRT site having the sequence of SEQ ID NO:4 and the second recombination site is a FRT site having the sequence of SEQ ID NO:8.

In an embodiment the first recombination site is a FRT site having the sequence of SEQ ID NO:4 and the second recombination site is a FRT site having the sequence of SEQ ID NO:9.

In an embodiment the first recombination site is a FRT site having the sequence of SEQ ID NO:4 and the second recombination site is a FRT site having the sequence of SEQ ID NO:10.

In an embodiment the first recombination site is a FRT site having the sequence of SEQ ID NO:4 and the second recombination site is a FRT site having the sequence of SEQ ID NO:1.

In an embodiment the first recombination site is a FRT site having the sequence of SEQ ID NO:4 and the second recombination site is a FRT site having the sequence of SEQ ID NO:2.

In an embodiment the first recombination site is a FRT site having the sequence of SEQ ID NO:4 and the second recombination site is a FRT site having the sequence of SEQ ID NO:3.

In an embodiment the first recombination site is a FRT site having the sequence of SEQ ID NO:5 and the second recombination site is a FRT site having the sequence of SEQ ID NO:6.

In an embodiment the first recombination site is a FRT site having the sequence of SEQ ID NO:5 and the second recombination site is a FRT site having the sequence of SEQ ID NO:7.

In an embodiment the first recombination site is a FRT site having the sequence of SEQ ID NO:5 and the second recombination site is a FRT site having the sequence of SEQ ID NO:8.

In an embodiment the first recombination site is a FRT site having the sequence of SEQ ID NO:5 and the second recombination site is a FRT site having the sequence of SEQ ID NO:9.

In an embodiment the first recombination site is a FRT site having the sequence of SEQ ID NO:5 and the second recombination site is a FRT site having the sequence of SEQ ID NO:10.

In an embodiment the first recombination site is a FRT site having the sequence of SEQ ID NO:5 and the second recombination site is a FRT site having the sequence of SEQ ID NO:1.

In an embodiment the first recombination site is a FRT site having the sequence of SEQ ID NO:5 and the second recombination site is a FRT site having the sequence of SEQ ID NO:2.

In an embodiment the first recombination site is a FRT site having the sequence of SEQ ID NO:5 and the second recombination site is a FRT site having the sequence of SEQ ID NO:3.

In an embodiment the first recombination site is a FRT site having the sequence of SEQ ID NO:5 and the second recombination site is a FRT site having the sequence of SEQ ID NO:4.

In an embodiment the first recombination site is a FRT site having the sequence of SEQ ID NO:6 and the second recombination site is a FRT site having the sequence of SEQ ID NO:7.

In an embodiment the first recombination site is a FRT site having the sequence of SEQ ID NO:6 and the second recombination site is a FRT site having the sequence of SEQ ID NO:8.

In an embodiment the first recombination site is a FRT site having the sequence of SEQ ID NO:6 and the second recombination site is a FRT site having the sequence of SEQ ID NO:9.

In an embodiment the first recombination site is a FRT site having the sequence of SEQ ID NO:6 and the second recombination site is a FRT site having the sequence of SEQ ID NO:10.

In an embodiment the first recombination site is a FRT site having the sequence of SEQ ID NO:7 and the second recombination site is a FRT site having the sequence of SEQ ID NO:8.

In an embodiment the first recombination site is a FRT site having the sequence of SEQ ID NO:7 and the second recombination site is a FRT site having the sequence of SEQ ID NO:9.

In an embodiment the first recombination site is a FRT site having the sequence of SEQ ID NO:7 and the second recombination site is a FRT site having the sequence of SEQ ID NO:10.

In an embodiment the first recombination site is a FRT site having the sequence of SEQ ID NO:6 and the second recombination site is a FRT site having the sequence of SEQ ID NO:1.

In an embodiment the first recombination site is a FRT site having the sequence of SEQ ID NO:6 and the second recombination site is a FRT site having the sequence of SEQ ID NO:2.

In an embodiment the first recombination site is a FRT site having the sequence of SEQ ID NO:6 and the second recombination site is a FRT site having the sequence of SEQ ID NO:3.

In an embodiment the first recombination site is a FRT site having the sequence of SEQ ID NO:6 and the second recombination site is a FRT site having the sequence of SEQ ID NO:4.

In an embodiment the first recombination site is a FRT site having the sequence of SEQ ID NO:6 and the second recombination site is a FRT site having the sequence of SEQ ID NO:5.

In an embodiment the first recombination site is a FRT site having the sequence of SEQ ID NO:8 and the second recombination site is a FRT site having the sequence of SEQ ID NO:9.

In an embodiment the first recombination site is a FRT site having the sequence of SEQ ID NO:8 and the second recombination site is a FRT site having the sequence of SEQ ID NO:10.

In an embodiment the first recombination site is a FRT site having the sequence of SEQ ID NO:8 and the second recombination site is a FRT site having the sequence of SEQ ID NO:1.

In an embodiment the first recombination site is a FRT site having the sequence of SEQ ID NO:8 and the second recombination site is a FRT site having the sequence of SEQ ID NO:2.

In an embodiment the first recombination site is a FRT site having the sequence of SEQ ID NO:8 and the second recombination site is a FRT site having the sequence of SEQ ID NO:3.

In an embodiment the first recombination site is a FRT site having the sequence of SEQ ID NO:8 and the second recombination site is a FRT site having the sequence of SEQ ID NO:4.

In an embodiment the first recombination site is a FRT site having the sequence of SEQ ID NO:8 and the second recombination site is a FRT site having the sequence of SEQ ID NO:5.

In an embodiment the first recombination site is a FRT site having the sequence of SEQ ID NO:8 and the second recombination site is a FRT site having the sequence of SEQ ID NO:6.

In an embodiment the first recombination site is a FRT site having the sequence of SEQ ID NO:8 and the second recombination site is a FRT site having the sequence of SEQ ID NO:7.

In an embodiment the first recombination site is a FRT site having the sequence of SEQ ID NO:9 and the second recombination site is a FRT site having the sequence of SEQ ID NO:1.

In an embodiment the first recombination site is a FRT site having the sequence of SEQ ID NO:9 and the second recombination site is a FRT site having the sequence of SEQ ID NO:2.

In an embodiment the first recombination site is a FRT site having the sequence of SEQ ID NO:9 and the second recombination site is a FRT site having the sequence of SEQ ID NO:3.

In an embodiment the first recombination site is a FRT site having the sequence of SEQ ID NO:9 and the second recombination site is a FRT site having the sequence of SEQ ID NO:4.

In an embodiment the first recombination site is a FRT site having the sequence of SEQ ID NO:9 and the second recombination site is a FRT site having the sequence of SEQ ID NO:5.

In an embodiment the first recombination site is a FRT site having the sequence of SEQ ID NO:9 and the second recombination site is a FRT site having the sequence of SEQ ID NO:6.

In an embodiment the first recombination site is a FRT site having the sequence of SEQ ID NO:9 and the second recombination site is a FRT site having the sequence of SEQ ID NO:7.

In an embodiment the first recombination site is a FRT site having the sequence of SEQ ID NO:9 and the second recombination site is a FRT site having the sequence of SEQ ID NO:8.

In an embodiment the first recombination site is a FRT site having the sequence of SEQ ID NO:9 and the second recombination site is a FRT site having the sequence of SEQ ID NO:10.

In an embodiment the first recombination site is a FRT site having the sequence of SEQ ID NO:10 and the second recombination site is a FRT site having the sequence of SEQ ID NO:1.

In an embodiment the first recombination site is a FRT site having the sequence of SEQ ID NO:10 and the second recombination site is a FRT site having the sequence of SEQ ID NO:2.

In an embodiment the first recombination site is a FRT site having the sequence of SEQ ID NO:10 and the second recombination site is a FRT site having the sequence of SEQ ID NO:3.

In an embodiment the first recombination site is a FRT site having the sequence of SEQ ID NO:10 and the second recombination site is a FRT site having the sequence of SEQ ID NO:4.

In an embodiment the first recombination site is a FRT site having the sequence of SEQ ID NO:10 and the second recombination site is a FRT site having the sequence of SEQ ID NO:5.

In an embodiment the first recombination site is a FRT site having the sequence of SEQ ID NO:10 and the second recombination site is a FRT site having the sequence of SEQ ID NO:6.

In an embodiment the first recombination site is a FRT site having the sequence of SEQ ID NO:10 and the second recombination site is a FRT site having the sequence of SEQ ID NO:7.

In an embodiment the first recombination site is a FRT site having the sequence of SEQ ID NO:10 and the second recombination site is a FRT site having the sequence of SEQ ID NO:8.

In an embodiment the first recombination site is a FRT site having the sequence of SEQ ID NO:10 and the second recombination site is a FRT site having the sequence of SEQ ID NO:9.

In an embodiment, the first and second insert nucleic acids are situated on the genomic polynucleotide wherein the distance between the first and second insert nucleic acids is less than 500 kb, 400 kB, 300 kb, 200 kb, 150 kb, 100 kb, 75 kb, 50 kb or 25 kb.

In an embodiment, in step b) the genomic polynucleotide is exposed to the recombinase by introducing a gene encoding FLP-recombinase into the host cell. The gene encoding FLP-recombinase is optionally introduced into the host cell in a plasmid under the control of an inducible promoter or a constitutive promoter. Where an inducible promoter is used, the plasmid pCP20, having the nucleic acid sequence of SEQ ID NO:13 may suitably be used.

In an embodiment, the gene encoding FLP-recombinase has a nucleic acid sequence having at least 80%, 85%, 90%, 95%, 98% or 99% identity to the sequence of SEQ ID NO:12. In an embodiment, the FLP-recombinase has an amino acid sequence at least 80%, 85%, 90%, 95%, 98% or 99% identical to the sequence of SEQ ID NO:11.

In an embodiment, the insert nucleic acid encodes at least one selection marker. However, the method of the invention is particularly useful when at least 2, 3, 4, 5 or 6 insert nucleic acids each encode a selection marker. In these cases, multiple selection markers can be removed from a genomic polynucleotide in a single step without the removal of regions of DNA between the selection markers by an unwanted recombination event. This benefit is particularly strong where the selection markers are located within 100, 75, 50, 25, 10, 5 or 2 kb of one another in the genomic polynucleotide.

In an embodiment, the genomic polynucleotide is from an *Escherichia, Neisseria, Shigella, Klebsiella, Xhantomonas, Salmonella, Yersinia, Lactococcus, Lactobacillus, Pseudomonas, Corynebacterium, Streptomyces, Streptococcus, Staphylococcus, Bacillus* or *Clostridium* species. However, it is clear that the method of the invention can be used to remove multiple insert nucleic acids from a genomic polynucleotide from any organism in cluding eukaryotic and prokaryotic organisms, plants, insects, yeast and mammalian organisms including mouse, rat, rabbit. The method of the invention is suitable where the genomic polynucleotide is from *E. coli*.

A further aspect of the invention is a genomic polynucleotide prepared by the method of the invention.

Following the execution of the process of the invention, at least a first and a second region of the genomic polynucleotide are recombinantly manipulated and two deletions of nucleic acid occur between the pairs of identical recombination sites. This results in the loss of one recombination site per pair and the intervening nucleic acid. The results is a host cell genome polynucleotide comprising a first recombinantly engineered site and a second recombinantly engineered site, wherein a first single recombination site is adjacent to the first recombinantly engineered region, and a second single recombination site is adjacent to the second recombinantly engineered region, wherein the first and second recombination sites have nucleotide sequences which share 90-98% identity with each other and with the nucleic acid sequence of any further recombination sites present in the host cell genome polynucleotide.

In an embodiment, the first and second recombinantly engineered regions are regions at which part of the host cell genome has been removed. In an embodiment, the first and second recombinantly engineered regions are sites at which an additional nucleic acid segment of over 20, 50, 100, 250 or 500 base pairs in length has been inserted. In an embodiment, the first and second recombination sites are recombination sites for a recombinase, for example a FLP recombinase, for example a FLP recombinase which has the amino acid sequence of SEQ ID NO:11.

In an embodiment, the first and second recombination sites are 30-50 or 40-50 base pairs in length, preferably 48 base pairs in length. In an embodiment, the first recombination site has a nucleic acid sequence of SEQ ID NO:1-10. As outlined above, it is envisaged that any of the recombination sites of SEQ ID NO:1-10 can be used with any other recombination site of SEQ ID NO:1-10 such that recombination occurs between the homologous pairs of recombination sites but not between heterologous pairs of recombination sites. Preferred combinations have a first recombination site having a sequence selected from the group of SEQ ID NO:1-6 used in combination with a second recombination site having a sequence selected from the group of SEQ ID NO:1-6 (wherein the second recombination site is different to the first recombination site).

In an embodiment, the method of the invention results in a host cell comprising a host cell genome polynucleotide containing a first recombinantly engineered region and a second recombinantly engineered region, wherein a first recombination site scar is adjacent to the first recombinantly engineered region and a second recombination site scar is adjacent to the second recombinantly engineered region; wherein the first and second recombination site scars have a different polynucleotide sequences which are less than 98% identical to each other and less than 98% identical to the polynucleotide sequence of any further recombination site scar present in the host cell genome polynucleotide.

In an embodiment, the first and second recombinantly engineered regions are regions at which part of the host cell genome has been removed. In an embodiment, the first and second recombinantly engineered regions are regions at which an additional nucleic acid segment of over 20, 50, 100, 250 or 500 base pairs in length has been inserted.

In an embodiment, the first and second recombination sites are recombination sites for a recombinase, for example a FLP recombinase, for example a FLP recombinase having the amino acid sequence of SEQ ID NO:11.

In an embodiment, the first and second recombination sites are 30-50 or 40-50 base pairs in length, preferably 48 base pairs in length. In an embodiment, the first recombination site has a nucleic acid sequence of SEQ ID NO:1-10. A second recombination site will have a different nucleic acid sequence which is optionally selected from SEQ ID NO:1-10. Combinations of first and second recombination sites both with SEQ ID NO:1-6 are preferred.

In an embodiment, the first and second recombination sites are separated by less than 500 kbases, 400 kbases, 300 kbases, 200 kbases, 150 kbases, 100 kbases, 75 kbases, 50 kbases, 25 kbases, 10 kbases, 5 kBases, 4 kbases, 3 kbases, 2 kbases, 1 kbase. The chances of intervening nucleic acid being unintentionally deleted if the method of the invention is not followed is higher where the first and second recombination sites are close. Therefore the method of the invention is more advantageous where the first and second recombination sites are closer.

In an embodiment, the genetic manipulations are in an *E. coli* genome, for example *E. coli* strain W3110. The genetic manipulation optionally involves the removal of a wca colonic acid cluster and optionally replacing it with insert DNA, for example a heterologous glycan cluster. The genetic manipulation optionally involves the deletion of a waaL gene and optionally replacing it with a pglB gene. The genetic manipulation optionally involves the deletion of at least part of an rfb cluster, for example at least part of an rfb O16 cluster. In an embodiment, at least 1, 2 or all 3 of a waaL gene, at least part of an rfb cluster and at least part of a wca colanic acid cluster are deleted. In an embodiment, at least 1, 2 or all 3 or a waaL gene, at least part of an rfb cluster and at least part of a wca colanic acid cluster are replaced by heterologous genes, optionally as describe above.

The invention also discloses a process for making a glycosylated protein comprising the steps of:
  a) Culturing the host cell of the invention under conditions suitable for the production of glycosylated protein and
  b) Isolating the glycosylated protein from the culture.

The production of engineered glycosylated proteins in bacterial host cells can require multiple manipulations of the host cell genomic polynucleotide in order to delete some host cell genes and to incorporate heterologous genes encoding the proteins required to make a designed glycosylated protein, for example a bioconjugate. The multiple recombinant manipulations of the host cell genome may introduce multiple genetic markers which it would be advantageous to remove. Thus the processes of the invention are particularly applicable to the construction of a host cell which is subsequently used for the production of glycosylated proteins, for example bioconjugates.

A further aspect of the invention is a prokaryotic genomic polynucleotide or a eukaryotic chromosome comprising at least two (for example 3, 4, 5, 6, 7, 8, 9 or 10) recombination site scars adjacent to at least two (for example 3, 4, 5, 6, 7, 8, 9 or 10) recombination regions, wherein each recombination site scar has a different polynucleotide sequence. Typically, the number of recombination site scars is equal to the number of recombination regions.

A further aspect of the invention is a process for engineering a host cell comprising the steps of;
  a) integrating a first polynucleotide cassette including a first selection marker flanked by a first pair of recombination sites;
  b) Removing the first selection marker by the action of a recombinase which recognises the first pair of recombination sites;
  c) integrating a second polynucleotide cassette including a second selection marker flanked by a second pair of recombination sites; and
  d) removing the second selection marker by the action of a recombinase which recognises the second pair of recombination sites;
  wherein the first pair of recombination sites have an identical nucleic acid sequence and the second pair of recombination sites have an identical nucleic acid sequence and the first and second pairs of recombination sites share 90-98% nucleic acid sequence identity.

In an embodiment, the recombinase of step b) and step d) is a FLP recombinase for example a FLP recombinase which has an amino acid sequence at least 80%, 85%, 90%, 95%, 98%, 99% or 100% identical to SEQ ID NO:7.

A further aspect of the invention is an engineered host cell obtainable by the process of the invention.

All references or patent applications cited within this patent specification are incorporated by reference herein.

The invention is further described in the following paragraphs:
  1. A method of removing at least two portions of insert nucleic acid from a genomic polynucleotide in a host cell, said method comprising the steps of:
     a) preparing the genomic polynucleotide comprising a first insert nucleic acid which is flanked by a pair of first recombination sites in the same orientation which are identical to each other and have a first nucleic acid sequence;
     b) exposing the genomic polynucleotide of step a) to a recombinase that recognises the first recombination sites such that the identical recombination sites recombine resulting in the excision of the first insert nucleic acid and one of the first recombination sites;
     c) inserting into the genomic polynucleotide of step b) a second insert nucleic acid flanked by a pair of second recombination sites in the same orientation wherein the second recombination sites are identical to each other and have a second nucleic acid sequence which shares no more than 98% sequence identity with the first nucleic acid sequence; and
d) exposing the genomic polynucleotide of step c) to a recombinase that recognises the second recombination sites such that the identical recombination sites recombine resulting in the excision of the second insert nucleic acid and one of the second recombination sites but without the removal of genomic polynucleotide sequence which is not flanked by identical recombination sites.

2. A method for removing at least two portions of insert nucleic acid from a genomic polynucleotide in a host cell, said method comprising the steps of:
a) preparing the genomic polynucleotide comprising at least a first and a second insert nucleic acids, wherein
i) the first insert nucleic acid is flanked by first recombination sites in the same orientation which are identical to each other and have a first nucleic acid sequence ii) the second insert nucleic acid is flanked by second recombination sites in the same orientation which are identical to each other and have a second nucleic acid sequence which shares no more than 98% sequence identity with the first nucleic acid sequence and iii) any further recombination sites have a nucleic acid sequence that shares no more than 98% sequence identity with the first or second nucleic acid sequences; and
b) exposing the genomic polynucleotide to a recombinase that recognises the first and second recombination sites such that the identical recombination sites recombine resulting in the excision of the insert nucleic acid flanked by identical recombination sites but without the removal of genomic polynucleotide sequence which is not flanked by identical recombination sites.

3. The method of paragraph 1 or 2, wherein the genomic polynucleotide is a prokaryotic genomic polynucleotide or a plasmid.

4. The method of paragraph 1 or 2 or 3 wherein the genomic polynucleotide is a eukaryotic chromosome.

5. The method of any one of paragraphs 1-4 wherein the first and second insert nucleic acids are selection markers.

6. The method of paragraph 5 wherein the first and second insert nucleic acids are selection markers encoding proteins that confer resistance to ampicillin, kanamycin, chloramphenicol, spectinomycin or gentamycin.

7. The method of any one of paragraphs 2-6 wherein step a) prepares a genomic polynucleotide comprising a third insert nucleic acid which is flanked by a set of identical third recombination sites having a third nucleic acid sequence which shares no more than 98% sequence identity with the first nucleic acid sequence, second nucleic acid sequence or the nucleic acid sequence of any further recombination sites.

8. The method of paragraph 7 wherein step a) prepares a genomic polynucleotide comprising a fourth insert nucleic acid which is flanked by a set of identical fourth recombination sites having a fourth nucleic acid sequence which shares no more than 98% sequence identity with the first nucleic acid sequence, second nucleic acid sequence, third nucleic acid sequence or the nucleic acid sequence of any further recombination sites.

9. The method of paragraph 8 wherein step a) prepares a genomic polynucleotide comprising a fifth insert nucleic acid which is flanked by a set of identical fifth recombination sites having a fifth nucleic acid sequence which shares no more than 98% sequence identity with the first nucleic acid sequence, second nucleic acid sequence, third nucleic acid sequence, fourth nucleic acid or the nucleic acid sequence of any further recombination sites.

10. The method of paragraph 9 wherein step a) prepares a genomic polynucleotide comprising a sixth insert nucleic acid which is flanked by a set of identical sixth recombination sites having a sixth nucleic acid sequence which shares no more than 98% sequence identity with the first nucleic acid sequence, second nucleic acid sequence, third nucleic acid sequence, fourth nucleic acid, fifth nucleic acid or the nucleic acid sequence of any further recombination sites.

11. The method of any one of paragraphs 2-5, wherein the genomic polynucleotide prepared in step a) comprises 3, 4, 5, 6, 7, 8, 9, or 10 insert nucleic acids each flanked with identical pairs of recombination sites wherein each pair of recombination sites share 90%-98% sequence identity with any other pair of recombination sites 12. The method of any one of paragraphs 1-11 wherein the recombination sites are 30-50 base pairs in length, preferably 48 base pairs in length.

13. The method of any one of paragraph 1-12 wherein the recombination sites are recognised by a recombinase, preferably a FLP-recombinase.

14. The method of any one of paragraphs 1-13 wherein the first and second insert nucleic acids are situated on the genomic polynucleotide wherein the distance between the first and second insert nucleic acids is less than 100 kb.

15. The method of any one of paragraphs 1-14 wherein the first and second recombination sites are flippase recognition target (FRT) sites or variant FRT sites.

16. The method of paragraph 15 wherein the first recombination site is a FRT site having the sequence 5'-gaagttcctattccgaagttcctattctctagaaagtataggaacttc-3' (SEQ ID NO:1).

17. The method of any one of paragraphs 15-16 wherein the second recombination site is a FRT variant site having the sequence of any one of SEQ ID NO:2, 3, 4, 5 or 6.

18. The method of any one of paragraphs 1-17 wherein in step b) the genomic polynucleotide is exposed to the recombinase by introducing a gene encoding FLP-recombinase into the host cell.

19. The method of paragraph 18 wherein the gene encoding FLP-recombinase has a nucleic acid sequence at least 80% identical to the sequence of SEQ ID NO:12.

20. The method of paragraph 18 wherein the FLP-recombinase has an amino acid sequence at least 80% identical to the sequence of SEQ ID NO:11.

21. The method of any one of paragraphs 18-20, wherein the gene encoding FLP-recombinase is introduced into the host cell in a plasmid under the control of an inducible promoter or a constitutive promoter.

22. The method of paragraph 21 wherein the plasmid contains a FLP-recombinase gene under the control of an inducible promoter.

23. The method of paragraph 21 wherein the plasmid is pCP20, having the nucleic acid sequence of SEQ ID NO:12.

24. The method of any one of paragraphs 1-23 wherein the inert nucleic acid encodes at least one selection marker.

25. The method of paragraph 24 wherein at least 2, 3, 4, 5 or 6 insert nucleic acids each encode a selection marker.

26. The method of any one of paragraphs 1-25 wherein the genomic polynucleotide is from an *Escherichia, Neisseria, Shigella, Klebsiella, Xhantomonas, Salmonella, Yersinia, Lactococcus, Lactobacillus, Pseudomonas, Corynebacterium, Streptomyces, Streptococcus, Staphylococcus, Bacillus* or *Clostridium* species.

27. The method of paragraph 26 wherein the genomic polynucleotide is from *E. coli*.

28. A host cell comprising a genomic polynucleotide prepared by the method of any one of paragraphs 1-27.

29. A host cell genome polynucleotide comprising a first recombinantly engineered region and a second recombinantly engineered region, wherein a first single recombination site is adjacent to the first recombinantly engineered region, and a second single recombination site is adjacent to the second recombinantly engineered region, wherein the first and second recombination sites have nucleotide sequences which share 90-98% identity with each other and optionally with the nucleic acid sequence of any further recombination sites present in the host cell genome polynucleotide.

30. The host cell genome polynucleotide of paragraph 29 wherein the first and second recombinantly engineered regions are regions at which part of the host cell genome has been removed.

31. The host cell genome polynucleotide of paragraph 29 or 30 wherein the first and second recombinantly engineered regions are regions at which an additional nucleic acid segment of over 20, 50, 100, 200, 300, 400 or 500 base pairs in length has been inserted.

32. The host cell genome polynucleotide of any one of paragraphs 29-31 wherein the first and second recombination sites and recombination sites for a recombinase.

33. The host cell genome polynucleotide of paragraph 32 wherein the recombinase is a FLP recombinase.

34. The host cell genome polynucleotide of paragraph 33 wherein the FLP recombinase has the amino acid sequence of SEQ ID NO:11.

35. The host cell genome polynucleotide of any one of paragraphs 29-34 wherein the first and second recombination sites are 30-50 base pairs in length, preferably 48 base pairs in length.

36. The host cell genome polynucleotide of paragraph 35 wherein the first recombination site has a nucleic acid sequence of any one of SEQ ID NO:1-10.

37. A host cell comprising a host cell genome polynucleotide containing a first recombinantly engineered region and a second recombinantly engineered region, wherein a first recombination site scar is adjacent to the first recombinantly engineered region and a second recombination site scar is adjacent to the second recombinantly engineered region; wherein the first and second recombination site scars have different polynucleotide sequences which are less than 98% identical to each other and optionally less than 98% identical to the polynucleotide sequence of any further recombination recombination site scar present in the host cell genome polynucleotide.

38. The host cell of paragraph 37 wherein the first and second recombinantly engineered regions are regions at which part of the host cell genome has been removed.

39. The host cell of paragraph 37 or 38 wherein the first and second recombinantly engineered regions are regions at which an additional nucleic acid segment of over 20, 50, 100, 200, 300, 400 or 500 base pairs in length has been inserted.

40. The host cell of any one of paragraphs 37-39 wherein the first and second recombination sites are recombination sites for a recombinase.

41. The host cell of paragraph 40 wherein the recombinase is a FLP recombinase.

42. The host cell of paragraph 41 wherein the FLP recombinase has the amino acid sequence of SEQ ID NO:11.

43. The host cell of any one of paragraphs 37-42 wherein the first and second recombination sites are 30-50 base pairs in length, preferably 48 base pairs in length.

44. The host cell of paragraph 43 wherein the first recombination site has a nucleic acid sequence of any one of SEQ ID NO:1-10.

45. The host cell of any one of paragraphs 37-44 wherein the first and second recombination sites are separated by less than 100 kbases, 75 kbases, 50 kbases, 25 kbases, 10 kbases, 5 kbases, 4 kbases, 3 kbases, 2 kbases or 1 kbase.

46. The host cell of paragraph 45 wherein the first and second recombination sites are separated by less than 5 kbases.

47. A prokaryotic genomic polynucleotide or a eukaryotic chromosome comprising at least two recombination recombination site scars adjacent to at least two recombinantly engineered regions, wherein each recombination site scar has a different polynucleotide sequence.

48. A process for engineering a host cell comprising the steps of;
    a) integrating a first polynucleotide cassette including a first selection marker flanked by a first pair of recombination sites;
    b) removing the first selection marker by the action of a recombinase which recognises the first pair of recombination sites;
    c) integrating a second polynucleotide cassette including a second selection marker flanked by a second pair of recombination sites; and
    d) removing the second selection marker by the action of a recombinase which recognises the second pair of recombination sites;
    wherein the first pair of recombination sites have an identical nucleic acid sequence and the second pair of recombination sites have an identical nucleic acid sequence and the first and second pairs of recombination sites share 90-98% nucleic acid sequence identity.

49. The process of paragraph 48 wherein the recombinase of step b) and d) is a FLP recombinase 50. The process of paragraph 49 wherein the FLP recombinase has an amino acid sequence at least 80% identical to SEQ ID NO:11.

51. An engineered host cell obtainable by the process of any one of paragraphs 48-50.

52. An engineered host cell comprising single copies of at least 2, 3, 4, 5, 6, 7, 8, 9 or 10 recombination sites in the host cell genomic polynucleotide, wherein each recombination site has a nucleotide sequence which is less than 98% identical to the other recombinations sites.

53. The engineered host cell of paragraph 52 wherein the at least 2 recombination sites are FRT sites.

54. The engineered host cell of paragraph 52 or claim 53 wherein the at least 2 recombination sites are separated by less than 100 kb, 75 kb, 50 kb, 25 kb, 10 kb, 5 kb, 3 kb or 1 kb in the host cell genomic polynucleotide.

55. An engineered Gram negative host cell in which at least part of a native rfb cluster and at least part of a wca colanic acid cluster have been deleted whilst maintaining intact a promoter of the rfb cluster.

56. The engineered Gram negative host cell of paragraph 53 wherein a waaL gene is also deleted.

57. The engineered Gram negative host cell of paragraph 53 or 54 wherein the gram negative host cell is *E. coli*.

58. The engineered Gram negative host cell of any one of paragraphs 53-55 wherein at least part of the native rfb cluster is replaced with a heterologous glycan cluster.

59. The engineered Gram negative host cell of any one of paragraphs 53-56 wherein the waaL gene is replaced with a pglB gene.

60. The host cell of any one of paragraphs 28 or 37-46 or 51-59 wherein the host cell is engineered to express a) an oligosaccharyltransferase, for example PglB or PglL; b) a heterologous glycan cluster, for example an rfb cluster or a gene cluster encoding glycosyltransferases required to synthesize a capsular polysaccharide; and a protein containing a glycosylation site recognised by the oligosaccharyltransferase, for example an optimized consensus sequence disclosed in WO 06/119987 (claim 1)

61. A process for making a glycosylated protein comprising the steps of;
    i) Culturing the host cell of paragraph 60 under conditions suitable for the production of glycosylated protein and
    ii) Isolating the glycosylated protein from the culture.

In order that this invention may be better understood, the following examples are set forth. These examples are for purposes of illustration only, and are not to be construed as limiting the scope of the invention in any manner.

EXAMPLES

Example 1: Use of Two Alternative FRT Pairs in Occasion of Strain Construction for *S. pneumoniae* Serotype 33F Capsular Polysaccharide Conjugate Production Strain stGVXN8661 is a derivative of *Escherichia coli* W3110 which contains several genomic modifications involving the use of FRTwt such that single FRTwt were present in three positions on the genomic DNA, adjacent to the sites of recombinant events.

Further genomic manipulation was used to delete further genes from stGVXN8661 while maintaining the rest of the genome intact. The selection marker needed to be removed in order to allow further modification of the strain.

The first steps regard the construction of pDOC plasmids to use for the deletion. p3910 and p3911 were prepared as follows. An insert was generated resulting from an assembly PCR using two PCR products and oligonucleotides pairs for cloning the HR2 and the clmR cassette into the donor plasmid pDOC-C. One PCR product was generated from pKD3 (GenBank: AY048742.1) using oligonucleotides encoding a clmR cassette and FRTwt sites and another was the 3' homology region derived from PCR of W3110 genomic DNA with oligonucleotides. The assembled DNA was cut using BamH1/EcoR1 and cloned into the same sites in pDOC-C, resulting in p482. A PCR product of the 5' homology region was then generated using W3110 chromosomal DNA and oligonucleotides, cut with BamHI and SpeI and cloned into the SpeI/BamHI sites of p482, resulting in p562. The nucleotide sequence of a multiple cloning site obtained by annealing of 5'-phosphorylated oligonucleotides was cloned via NheI and BamHI into p562, resulting in p1043. Kanamycin resistance cassette (kanR) flanked by two FRT3 sites has been synthetized and cloned into pUC57 (GenBank: Y14837.1) by Genewiz LCC, resulting in p3268. The NdeI/BstBI fragment from p3268 containing FRT3-kanR-FRT3 has been cloned into p1043, substituting FRTwt-clmR-FRTwt, resulting in p3602. The 5' homology region of p1043 and p3602 has been replaced by cloning via SpeI/NheI a new 5' 1276-bp homology region, resulting in p3910 and p3911, respectively.

p3910 and p3911 encode the 5' and 3' homology regions with an MCS and an inverted clmR resistance cassette flanked by two FRTwt sites, and a kanR resistance cassette flanked by two FRT3 sites, respectively in between. These resulting plasmids were the donor plasmid for the deletion of the selected genomic sequence and their replacement with FRTwt-clmR-FRTwt or with FRT3-kanR-FRT3.

For the deletion a helper plasmid is needed. A variant of pTKRED (GenBank: GU327533.1) p2824 was used.

Deletions and selection. Two parallel deletions procedure have been carried out on strain stGVXN8661. The two procedures differ for the usage of p3910 or p3911 as donor plasmids, and for the resistance applied for the selection: chloramphenicol when p3910 was used and kanamycin when p3911 was used. Strain stGVXN8661 was co-transformed with p2824 and the donor plasmid via electroporation. Because of the temperature sensitive replication phenotype of p2824, resulting cells were grown at 30° C. at all times in LB supplemented with spectinomycin for selection of p2824 and with chloramphenicol or kanamycin for selection of p3910 and p3911, respectively. The plasmids were inserted into the acceptor cells to enable the expression of the enzymes encoded on the helper plasmid in the presence of the donor plasmid DNA within the same cell.

Next, the insertion procedure was performed. The freshly transformed strains were grown in TSB medium in the presence of ampicillin and spectinomycin at 30° C. at 5 ml scale overnight at 180 rpm. 50 μl of the dense culture was transferred to a new tube containing 1 ml TSB supplemented with spectinomycin and chloramphenicol or kanamycin. The new culture was then grown at 180 rpm for 2 hrs at 30° C., the cells were centrifuged at 4000 rpm for 15 minutes at 4° C., and the supernatant was replaced by TSB medium supplemented with spec, 0.2% arabinose (w/v), and 1 mM IPTG. The media composition supports helper plasmid selection, and recombinase and SceI endonuclease expression to enable insertion. The cells were resuspended and further incubated at 30° C. for 3 hrs at 180 rpm. 50 μl of those culture were used to inoculate 1 ml TSB supplemented with 0.2% arabinose (w/v), and 1 mM IPTG, which was grown overnight at 30° C. at 180 rpm. The absence of resistance in this step enhance the loss of the helper plasmid.

0.5 ml of the culture was plated on TSB plates supplemented with clm or kan, depending on the donor plasmid used (for selection of the DNA insert) and 10% (w/v) sucrose (to counterselect against the donor plasmid) and incubated at 37° C. overnight (to select for loss of the temperature sensitive helper plasmid).

A lawn of cells appeared for both procedures. Streak outs were made on TSB plates supplemented with clm or kan, depending on the donor plasmid used and again incubated at 37° C. overnight.

To screen the resulting colonies for the correct insertion phenotype, single colonies from the streak outs were replica plated onto LB plates supplemented with spec, amp, or clm when p3910 was used or onto LB plates supplemented with spec, amp, or kan when p3911 was used. Colonies resistant to clm or kan (for presence of the insert), but sensitive for amp and spec (for absence of the donor and helper plasmids) were further analyzed for the insertion.

To confirm that the strain lost the replaced DNA originating from W3110, and contained the DNA insert, colony PCR was performed. Candidate colonies with the correct phenotype were picked and underwent a colony PCR test. Three PCR were executed. i) One PCR amplifies the region at the 5' of the inserted DNA only if the recombination happened correctly. Used oligonucleotides are 4897/3233 for integration with p3910 and 4897/4363 for integration with p3911. ii) One PCR amplifies the region at the 3' of the inserted DNA only if the recombination happened correctly. Used oligonucleotides are 3315/3208 for integration with p3910 and 4364/3208 for integration with p3911. iii) One PCR amplifies the genomic region which has been substituted, meaning that the correctly modified strain should not give any product while the unmodified strain should. Used oligonucleotides are 3213/3208. Various clones from both integrations showed the right PCR pattern (PCR i and ii positive, PCR iii negative). The resulting strains were designated st8661 Δ::FRTwt-clmR-FRTwt (st10851) when p3910 was used as a donor plasmid and st8661 Δ::FRT3-kanR-FRT3 (st10852) when p3911 was used as a donor plasmid.

The following step is the removal of the antibiotic resistance from the integrated strains to obtain a "markerless" deletion of wbbIL. The two obtained strains were transformed with the temperature sensitive pCP20 plasmid expressing the FLP recombinase [1] and plated on LB plates supplemented with ampicillin to select for pCP20. Plates were incubated overnight at 30° C. in order to allow the replication of the plasmid. 5 ml LB cultures were inoculated with streaks from plates and grown overnight at 42° C. to ensure loss of pCP20. Serial dilutions from the overnight cultures were plated on LB plates. Single colonies were replicated on LB plates supplemented with ampicillin, chloramphenicol, or without antibiotics when derived from st8661 Δ::FRTwt-clmR-FRTwt or on LB plates supplemented with ampicillin, kanamycin, or without antibiotics when derived from st8661 Δ::FRT3-kanR-FRT3. In both case 100% of the colonies grew only on plates devoid of antibiotics, indicating that in both situations the resistance cassette was removed by the pCP20-encoded FLP recombinase.

In order to understand whether the FLP-removed DNA was limited to the FRT-flanked inserted resistance cassette, a colony PCR was carried out. The used oligonucleotides 4897/2174 result in a 2781-bp product if the resistance is removed and the border regions are present. No bands are expected if the region between the newly inserted FRT and the FRTwt present in the upstream wca locus is lost. It was observed the correct band only when the resistance was removed from Δ::FRT3-kanR-FRT3, indicating that FRT crossreactivity does not happen between the FRTwt site of the wca locus and the newly introduced FRT3. Conversely, when FRTwt are introduced, cross reactivity with the other FRTwt site present in the wca locus causes the loss of genomic material between the two sites. The strain resulting from kanamycin resistance cassette from st8661 Δ::FRT3-kanR-FRT3 (st10852) is named st10853.

To check if production of Sp33F glycoconjugate by strain st10852 and st10853 is comparable to what observed in st8661, the following experiment has been carried out. Strains st8661, st10852, and st10853 have been transformed via electroporation with plasmids 3914, encoding the carrier protein, rcsA from *E. coli* K30, chain length regulator, wzy, all under IPTG-inducible promoter, and with plasmid 3750, encoding constitutively expressed genes wchA, and genes from wciB to wzy of the 33F cluster. Production cells were inoculated into 5 ml TB-dev medium supplemented with 10 mM MgCl$_2$, spectinomycin, and tetracyclin and grown overnight at 37° C. into stationary phase. Cells were then diluted to an OD$_{600}$ of 0.05 in 50 ml TBdev containing 10 mM MgCl$_2$, spectinomycin, tetracyclin, and 0.01 mM IPTG. After 6 hours, 0.09 IPTG was added to the cultures, which were then grown overnight at 37° C. IPTG drives the expression of the elements encoded in p3814 (including the carrier protein and rcsA, which drives the expression of the 33F capsular polysaccharide cluster in the wca locus), and the genome-integrated pglB. Cells were then harvested by centrifugation and periplasmic cell extracts were prepared using the Lysozyme method [2]. Periplasmic extracts (normalized to OD$_{600}$) were separated by SDS PAGE and analyzed by immunoblotting after electrotransfer (FIG. 1). Detection with the anti His antiserum (left panel) and anti 33F antiserum (right panel) both show a clear ladder like pattern between 70 to 170 kDa for all samples, strongly indicative of glycoproteins consisting of the carrier protein and 33F polysaccharide. The amount and quality of glycoconjugate obtained from st10852 and from st10853 is comparable to what observed in st8661. This indicates that the genes upstream of the deleted region are still present and active.

Strain st10853 has been used for bioreactor-scale 33F bioconjugate production. Moreover, the strain's genome has been further modified via an analogous procedure, and a final resistance-free strain has been achieved.

Example 2: Systematic Study on Usage of Alternative FRT Sites for Contemporary Excision of Neighboring Resistance Cassettes A series of *E. coli* W3110 derivatives have been constructed, differing only for the presence of alternative FRT sequences. Firstly the O16 rfb cluster has been replaced by a gentamycin resistance cassette gntR, in the same orientation of the substituted cluster, followed by a chloramphenicol resistance cassette clmR in the opposite orientation and enclosed between two FRTwt sites. Secondly, six parallel homologous recombinations have been carried out in order to replace the colanic acid wca cluster with a kanamycin resistance cassette kanR in the opposite orientation of the replaced cluster, enclosed between two FRTwt, FRT3, FRT10, FRT13, FRT14, and FRT15 sites, resulting in strain 10175, 10176, 10177, 10178, 10179, and 10180, respectively.

Figure 2:
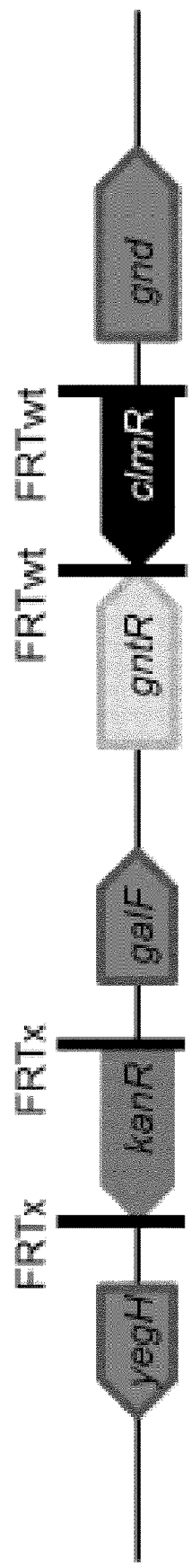
FIG. 2—Scheme of genomic organization of replaced wca and rfb clusters in strains 10175 and 10180.

The six strains are able to grow in media containing kanamycin, gentamycin, and chloramphenicol. FIG. 2 describes the genetic organization of the wca and rfb loci in the six strains.

In order to evaluate the degree of cross reactivity of the FRTwt site with the alternative FRT sites, a resistance cassette removal protocol has been applied to the six strains. The strains were transformed with the temperature sensitive pCP20 plasmid expressing the FLP recombinase [1] and plated on LB plates supplemented with ampicillin to select for pCP20. Plates were incubated overnight at 30° C. in order to allow the replication of the plasmid. 5 ml LB cultures were inoculated with streaks from plates and grown over weekend at 37° C. to ensure loss of pCP20. Serial dilutions from the dense cultures were plated on LB plates. Sixty single colonies per recombination were replicated on LB plates supplemented with ampicillin, kanamycin, chloramphenicol, gentamycin, or without antibiotics and grown overnight at 37° C.

In case of cross-reaction between the FRT sites flanking the chloramphenicol cassette and the ones flanking the kanamycin resistance cassette, the loss of resistance against kanamycin, gentamycin, and chloramphenicol is expected. In case of lack cross-reactivity, gentamycin resistance should be retained, while kanamycin and chloramphenicol resistance should be lost. Persistence of kanamycin resistance can be explained with sub-optimal efficiency of the FRT sites flanking the corresponding cassette. Persistence of chloramphenicol resistance can be explained either by a sub-optimal efficiency of the FRTwt pair, or by the retention of pCP20, which is both ampicillin and chloramphenicol resistant. In the last scenario, concomitant persistence of the ampicillin resistance is expected.

The resistance pattern of the replicated clones was observed and it is summarized in Table 1. In general, five different phenotypic patterns have been observed, ignoring the ampicillin resistance situation: pattern A: the clone is resistant to kanamycin, gentamycin, and chloramphenicol, indicating complete lack of FLP recombinase activity on both FRT pairs; pattern B: no resistance left, indicating unspecific cross-reaction between the two FRT pairs; pattern C: resistance to kanamycin and gentamycin, indicating defective FLP recombinase activity on FRT pair flanking kanR; pattern D: resistance to chloramphenicol and gentamycin, indicating either defective activity of the FLP recombinase on the FRTwt pair flanking clmR or correct specific removal of kanR and clmR without cross reaction between the FRT pairs flanking clmR and kanR but persistence of plasmid pCP20; pattern E: resistance to gentamycin only, indicating correct specific removal of kanR and clmR without cross reaction between the FRT pairs flanking clmR and kanR.

of the clones derived from strain 10175 (FRTwt flanking both clmR and kanR) show this pattern. Pattern C (kanamycin and gentamycin resistance left) was observed in few cases when FRT10, FRT13, and FRT15 flank kanR. This might indicate a slightly inferior efficiency of the FLP recombinase in acting on these specific FRT sites. Pattern D (gentamycin and chloramphenicol resistance left), was observed in a number of cases when FRT3, FRT10, FRT13 and FRT14 flank kanR. With the exception of one clone derived from st10176 (FRT3) all the clones presenting pattern D are also ampicillin resistant, suggesting a high likelihood that the chloramphenicol-resistant phenotype is due to the persistence of pCP20 rather than to a defective removal of clmR.

These results show that loss of DNA between neighboring FRTwt pairs is highly likely (93% of cases), while the likelihood significantly decreases if one of the two FRTwt pairs is replaced by a pair of alternative FRT sites. The excision of the gentamycin resistance was observed only in one case out of 300 when any of the alternative FRT sites was flanking kanR, underlining the specificity of the FLP-catalyzed reaction. The percentage of correct genetic pattern (only gentamicin cassette remaining) when alternative FRT sites have been used can be inferred from the phenotype. Phenotypic pattern E can only be explained with the genetic scenario in which a correct specific removal of the two cassettes happened, while phenotypic pattern D can be explained by the same (only when ampicillin resistant is also present) or by the lack of excision of clmR. Thus clones belonging to phenotypic pattern E represent the minimum possible number of clones in which the correct specific removal of both clmR and kanR without loss of gntR, while clones belonging to pattern E+D represent the maximum possible number of clones in which this genetic organization exists. Table 1 summarizes the percentage of clones with the right genetic pattern taking into account these considerations.

TABLE 1

Observed resistance patterns following FLP-mediated resistance removal in six different strains.

| kanR-flanking FRT's | N. of colonies per antibiotic plate. Tot: 60 colonies per FRT | | | | N. of colonies belonging to resistance pattern. Tot: 60 colonies per FRT | | | | | %[a] |
|---|---|---|---|---|---|---|---|---|---|---|
| | Amp$^R$ | Kan$^R$ | Clm$^R$ | Gnt$^R$ | A | B | C | D | E | |
| FRTwt | 0 | 0 | 0 | 4 | 0 | 56 | 0 | 0 | 4 | 7 |
| FRT3 | 28 | 0 | 26 | 60 | 0 | 0 | 0 | 27 | 33 | 55 to 98 |
| FRT10 | 7 | 4 | 4 | 60 | 0 | 0 | 4 | 4 | 52 | 87 to 93 |
| FRT13 | 20 | 10 | 19 | 59 | 1 | 1 | 9 | 18 | 31 | 52 to 82 |
| FRT14 | 5 | 0 | 1 | 60 | 0 | 0 | 0 | 1 | 59 | 98 to 100 |
| FRT15 | 0 | 14 | 0 | 60 | 0 | 0 | 14 | 0 | 46 | 77 |

[a]Percentage of colonies with only gentamycin cassette left.

Pattern A (no resistance removed) was observed only for one clone when strain 10178, where kanR is flanked by FRT13 sites, was used. Pattern B (all resistances removed) was almost exclusively observed for strain 10175, where kanR is flanked by FRTwt, representing 93% of clones for the resistance removal from this strain. The only exception is one clone derived from strain 10178, where FRT13 flank kanR. Pattern E (only gentamycin resistance left) was always observed in more than 50% of cases for all the strains for which alternative FRT sites flank kanR, while only 7%

Figure 3:
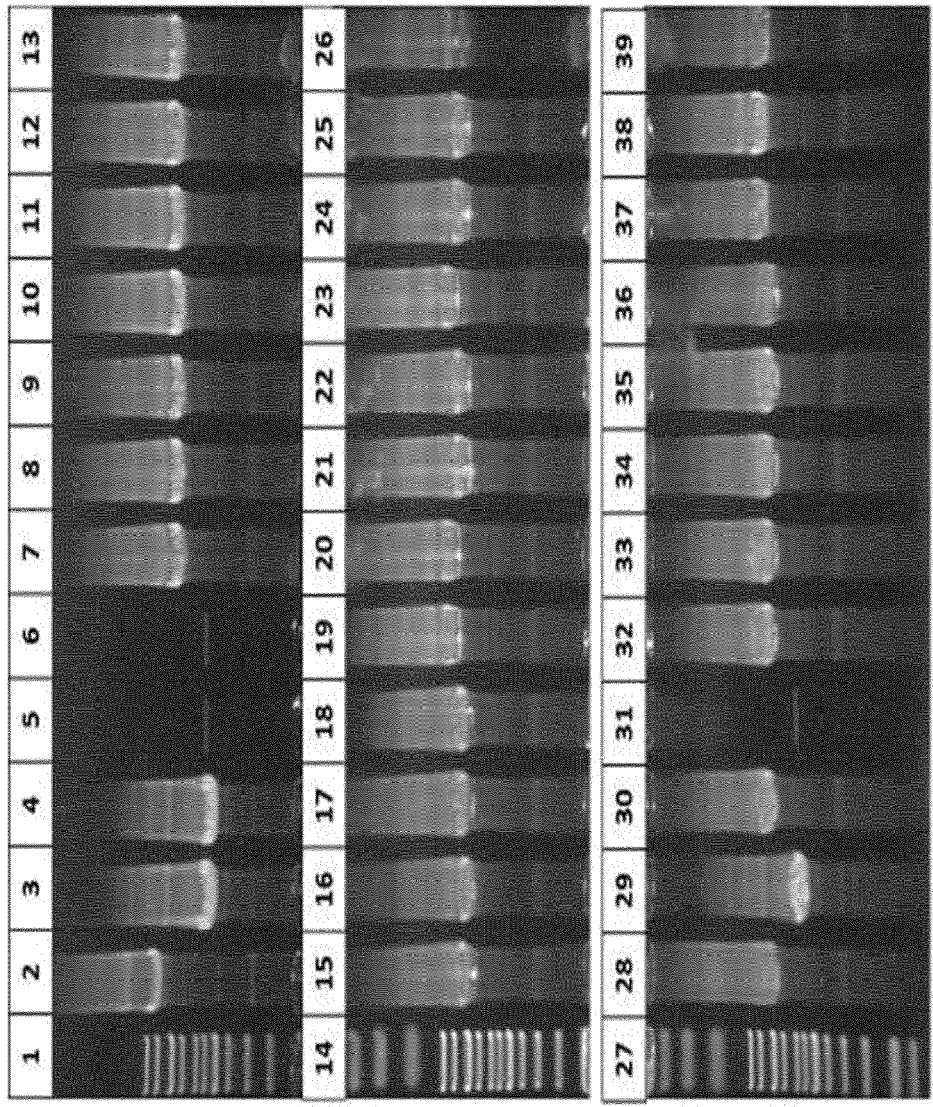
FIG. 3—Colony PCR on selected clones derived from FLP-mediated resistance cassette removal from strains 10175 to 10180. Lanes 1, 14 and 27 contain GeneRuler™ 1 kb DNA ladder, lane 2 contains St10175 before removal, lanes 3 and 4 contain FRTwt, pattern B, lanes 5 and 6 contain FRTwt pattern E, lanes 7, 8 and 9 contain FRT3, pattern E, lanes 10, 11 and 12 contain FRT3, pattern D, lanes 13, 15 and 16 contain FRT10, pattern E, lanes 17 and 18 contain FRT10, pattern D, lanes 19 and 20 contain FRT10, pattern C, lanes 21 and 22 contain, FRT13, pattern E, lane 23 contains FRT13, pattern A, lanes 24 and 25 contain FRT13, pattern D, lanes 26 and 28 contain FRT13, pattern C, lane 29 contains FRT13, pattern B, lanes 30, 31, 32 and 33 contain FRT14, pattern E, lane 34 contains FRT14, pattern D, lanes 35 and 36 contain FRT15, pattern E and lanes 37, 38 and 39 contain FRT15, pattern C.

To confirm the genetic organization of the clusters after the FLP-mediated resistance removal, a colony PCR has been carried out on selected clones belonging to different phenotypic patterns for each tested strain. The use of oligonucleotides 3206/3208 result in a 7922-bp product if no resistances have been removed, in a 3388-bp product if the whole genomic region between the two FRT sites has been removed, in a 6990-bp product if only clmR is excided, in a 6550-bp product if only kanR is excised, and in a 5618-bp product if the wanted pattern in which gntR only is left is achieved. All clones tested belonging to pattern D show band corresponding to the excision of both clmR and kanR, and not to the excision of kanR only. The observed product lengths for clones showing unambiguous resistance patterns (A, B, C, or E) correspond to the only possible inferred genetic pattern, with the following exceptions. Two out of four clones showing pattern E derived from the strains in which FRTwt flanks both clmR and kanR were assayed, but no PCR product was observed. Four clones belonging to pattern E from strain 10179 (FRT14) were tested, and one of them did not show any PCR product. The only colony belonging to pattern A when alternative FRT sites have been used derives from the strain bearing FRT13, and shows a product of length fitting with the removal of clmR only (6990 bp) rather than to the expected 7922-bp band, observed in the control, when no resistance is removed. One clone derived from the strain with FRT13 showed phenotypic pattern C, but the PCR shows a band of length corresponding to the removal of both clmR and kanR instead (FIG. 3).

Figure 4:
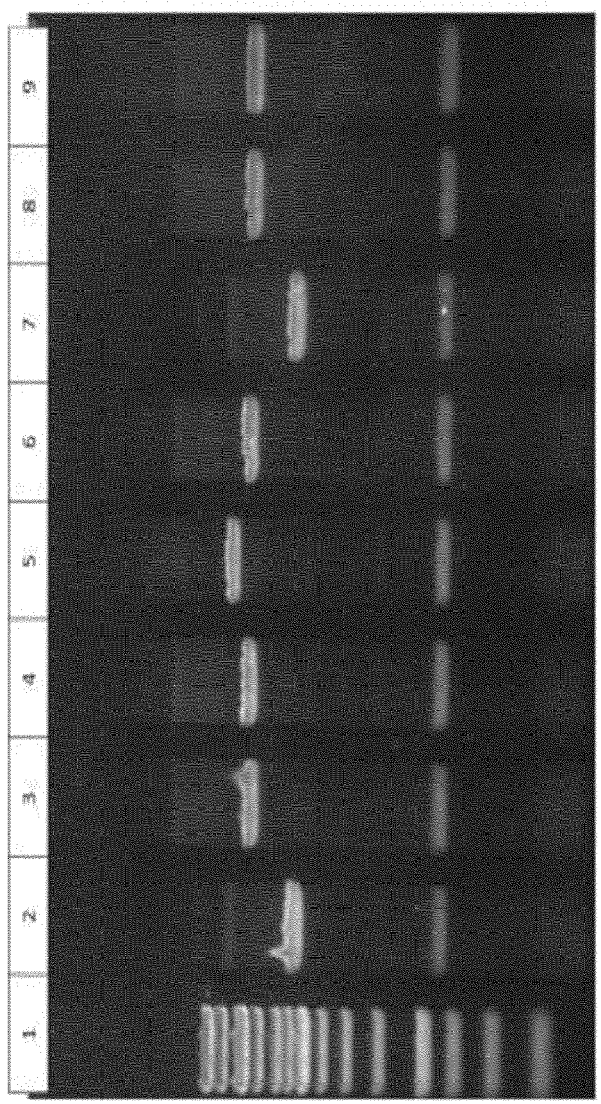
FIG. 4—Preparative PCR on genomic DNA strains derived from FLP-mediated resistance cassette removal.
Figure 5:
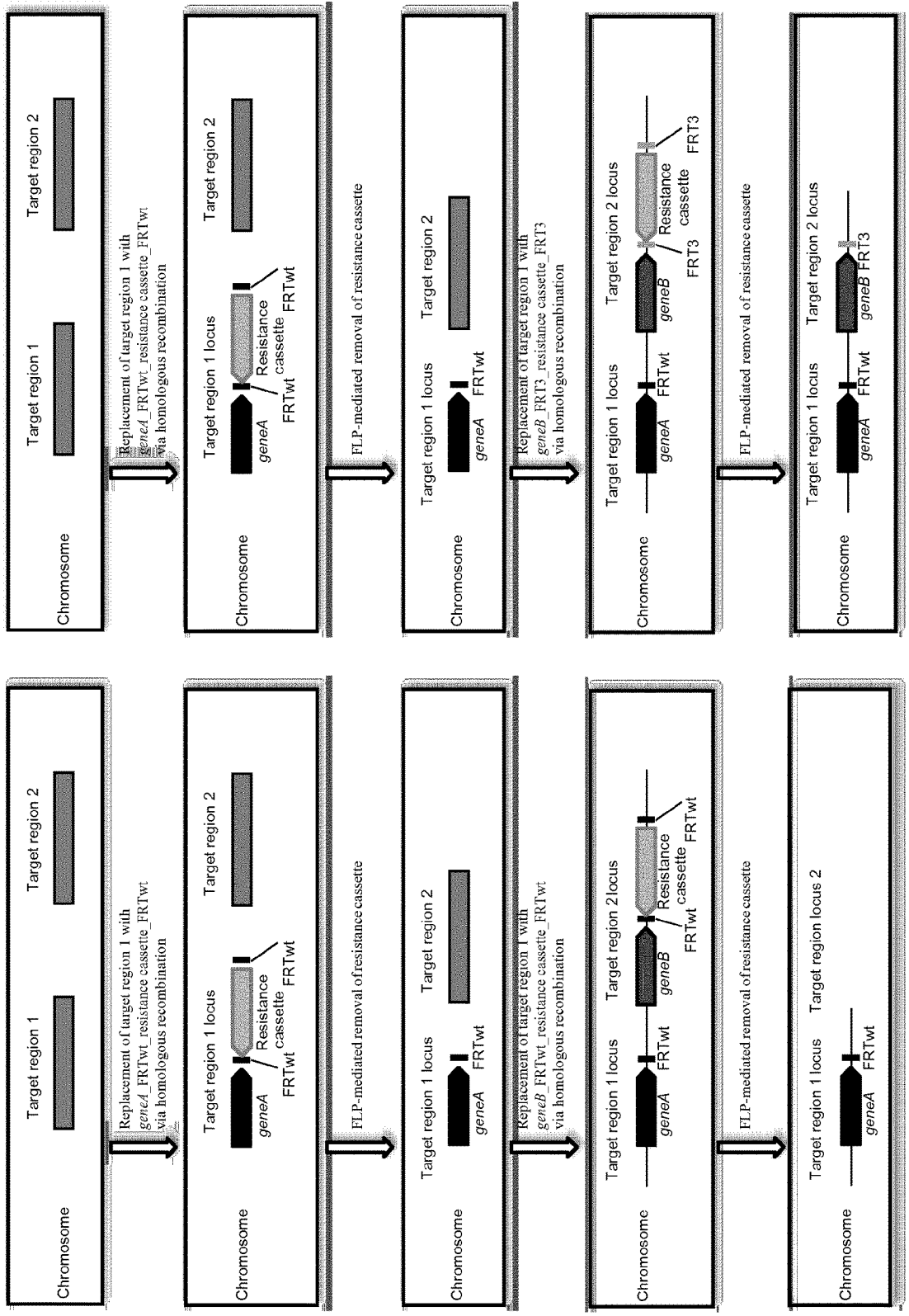
FIG. 5.—Concept scheme demonstrating the advantage of using alternative FRT sites.

One clone derived from the FRTwt-only bearing strain with pattern B, one clone derived from the FRT3 bearing strain with pattern E, one clone derived from the FRT10 bearing strain with pattern E, one clone derived from the FRT10 bearing strain with pattern C, one clone derived from the FRT13 bearing strain with pattern E, one clone derived from the FRT13 bearing strain with pattern B, one clone derived from the FRT14 bearing strain with pattern E, and one clone derived from the FRT15 bearing strain with pattern E have been stored and named 10247, 10248, 10249, 10250, 10251, 10252, 10253, 10254, respectively. For these 8 strains, genome has been isolated and a PCR using oligonucleotides 3206/3208 has been carried out. The PCR products have been purified and sequenced. The obtained product lengths (FIG. 4) and the sequencing results obtained further confirm the expected genomic organization. In the only strain in which a complete removal of the genomic material between the two FRT pairs is observed when using an alternative FRT site (FRT13, strain 10525), the only FRT site left is FRTwt.

This experiment proves that using alternative FRT sites is a valid and efficient approach for the excision of resistance cassettes from genomic regions neighboring an already existing FRTwt site without loss of enclosed DNA.

Example 3: Use of Alternative FRT Sites During Strain Development for a Further *S. pneumoniae* Serotype Capsular Polysaccharide Conjugate Production Strain stGVXN9876 is a derivative of *Escherichia coli* W3110 which contains several genomic modifications involving the use of FRTwt such that single copies of FRTwt were present in three positions on the genomic DNA, adjacent to the sites of recombinant events.

The aim of the genomic manipulation was to add copies of the glycosyl transferases from a *S. pneumoniae* glycan cluster and of the gne epimerase from *C. jejuni*.

The first steps regard the construction of pDOC plasmids to use for the replacement. p3408 was prepared as follows. A PCR product of the 5' homology region (containing 1.2 kb upstream the first gene of the wca cluster, wza) was obtained from *E. coli* W3110 genome by using oligonucleotides, and cloned into EcoRI/XhoI sites of pDOC-C, resulting in p693. A PCR product of the 3' homology region (containing 1.2 kb downstream the last gene of the wca cluster, wcaM) was obtained from *E. coli* W3110 genome using the oligonucleotides and cloned into the BcuI/NheI sites of p693, resulting in p699. A multiple cloning site was cloned into AscI/BamHI sites of p699, resulting in p3259. Plasmid 3914 was obtained from Genewiz LCC as gene synthesis service. The PCR product from p3914 with oligonucleotides 4110/4111, containing a kanamycin resistance cassette kanR, flanked by two FRT13 sites, was cloned into the HindIII site of p3259, resulting in p3306. Plasmid 3256 encodes genes encoding *S. pneumoniae* glycosyltransferases originating from PCR on the *S. pneumoniae* glycan cluster under control of the synthetic promoter J23114 and followed by the transcriptional terminator rrnb T2. This expression cassette was amplified and cloned into the PacI/XmaI sites of p3375, in the opposite direction relative to kanR. Plasmid 207, encoding gne previously amplified from *Campylobacter jejuni* genome, was used as a template for a PCR. The resulting amplicon contains the synthetic promoter J23100, added with one oligonucleotide, upstream gne, and it was cloned into the SbfI/XmaI site of p3375, resulting in p3408.

p3408 encodes the 5' and 3' homology regions for insertion in the wca cluster and between them, in the opposite orientation, the following elements: J23114 promoter, *S. pneumoniae* glycosyltransferase genes, rrnb T2 terminator, J23100 promoter, gne.

For the replacement, strain 9876 was co-transformed with pTKRED (GenBank: GU327533.1) and the donor plasmid p3408 via electroporation. Because of the temperature sensitive replication phenotype of pTKRED, resulting cells were grown at 30° C. at all times in LB supplemented with spectinomycin for selection of pTKRED and with kanamycin for selection of p3408. The plasmids were inserted into the acceptor cells to enable the expression of the enzymes encoded on the helper plasmid in the presence of the donor plasmid DNA within the same cell.

Next, the insertion procedure was performed. The freshly transformed strain was grown in TSB medium in the presence of kanamycin and spectinomycin at 30° C. at 5 ml scale overnight at 180 rpm. 50 µl of the dense culture was transferred to a new tube containing 1 ml TSB supplemented with spectinomycin and kanamycin. The new culture was then grown at 180 rpm for 2 hrs at 30° C., the cells were centrifuged at 4000 rpm for 15 minutes at 4° C., and the supernatant was replaced by TSB medium supplemented with spec, 0.2% arabinose (w/v), and 1 mM IPTG. The media composition supports helper plasmid selection, and recombinase and SceI endonuclease expression to enable insertion. The cells were resuspended and further incubated at 30° C. for 3 hrs at 180 rpm. 0.5 ml of the culture was plated on TSB plates supplemented with kan (for selection of the DNA insert) and 10% (w/v) sucrose (to counterselect against the donor plasmid) and incubated at 37° C. overnight (to select for loss of the temperature sensitive helper plasmid). A lawn of cells appeared. Streak outs were made on TSB plates supplemented with kan and incubated at 37° C. overnight.

To screen the resulting colonies for the correct insertion phenotype, single colonies from the streak outs were replica plated onto LB plates supplemented with spec, amp, or kan. Colonies resistant to kan (for presence of the insert), but sensitive for amp and spec (for absence of the donor and helper plasmids) were further analyzed for the insertion.

To confirm that the strain lost the replaced DNA originating from W3110, and contained the DNA insert, colony PCR was performed. Candidate colonies with the correct phenotype were picked and underwent a colony PCR test. Two PCR were executed. i) One PCR uses oligonucleotides 3206/4195 and amplifies the region at the 5' of the inserted DNA only if the recombination happened correctly. ii) One PCR uses oligonucleotides 3081/3957 and amplifies the region at the 3' of the inserted DNA only if the recombination happened correctly. Various clones from the integration showed the right PCR pattern (PCR i and ii positive). The resulting strain was designated st10084.

The following step is the removal of the antibiotic resistance from the integrated strain. Strain 10084 was transformed with the temperature sensitive pCP20 plasmid expressing the FLP recombinase [1] and plated on LB plates supplemented with ampicillin to select for pCP20. Plates were incubated overnight at 30° C. in order to allow the replication of the plasmid. 5 ml LB cultures were inoculated with streaks from plates and grown overnight at 42° C. to ensure loss of pCP20. Serial dilutions from the overnight cultures were plated on LB plates. 60 single colonies were replicated on LB plates supplemented with ampicillin, kanamycin, or without antibiotics. All the colonies grew on plates without antibiotic, 5 colonies grew on kanamycin plates (resistance cassette was not excised), 14 colonies grew on ampicillin plates (pCP20 was retained).

In order to confirm that the loss of kanamycin resistance is due to the excision of the cassette, and that no genomic material except the kanamycin resistance cassette has been lost, a colony PCR was carried out. Using oligonucleotides 3081 and 3957 is expected: i. a 1513-bp band if the kanamycin cassette is removed and the DNA bordering the FRT sites is not removed; ii. a 2879-bp band if the kanamycin cassette has not been removed; iii. no PCR product if the DNA region between the FRT13 site and the FRTwt site present in the rfb O16 locus has been looped out.

12 colonies with the right resistance pattern (no ampicillin and kanamycin resistance) were tested by colony PCR, and all of them showed the 1513-bp band expected if kanamycin resistance cassette is excised and the DNA between the FRT13 and FRTwt sites is intact. As a control, the strain before the resistance removal showed the expected 2879-bp band.

The usage of two alternative FRT site pairs (FRT13 for the wca locus replacement, FRTwt for the rfb locus replacement) allowed obtaining a double markerless integration without loss of DNA in these two adjacent loci. The resulting strain was named 10085.

Example 4: Use of Alternative FRT Sites to Introduce Further Recombinant Changes in a Strain Already Containing Single FRTwt Copies Strain stLMTB11280 is a derivative of *Eschericha coli* W3110 which contains several genomic modifications involving the use of FRTwt such that copies of FRTwt are present in multiple positions on the genomic DNA, adjacent to the sites of recombinant events. Two single copies of FRTwt were present as well as a pair of FRTwt sequences flanking a chloramphenicol resistance cassette.

Further genomic manipulations were carried out to add a copy of an engineered cluster in the genome.

The donor pDOC plasmid pLMTB4184 encodes the 5' and 3' homology regions for the replacement of genes from rfbD to wbbL of the O16 antigen cluster. In between them, in the same orientation, a transcription unit encoding seven genes of interest followed by a kanamycin resistance cassette in the opposite orientation flanked by two FRT3 sites.

For the replacement, strain 11280 was co-transformed with pTKRED (GenBank: GU327533.1) and the donor plasmid p4184 via electroporation. Because of the temperature sensitive replication phenotype of pTKRED, resulting cells were grown at 30° C. at all times in TSB supplemented with 10 mM MgCl$_2$, spectinomycin for selection of pTKRED and with kanamycin for selection of p4184. The plasmids were inserted into the acceptor cells to enable the expression of the enzymes encoded on the helper plasmid in the presence of the donor plasmid DNA within the same cell.

Next, the insertion procedure was performed. The freshly transformed strain was grown in TSB medium 10 mM MgCl$_2$ in the presence of kanamycin and spectinomycin at 30° C. at 5 ml scale overnight at 180 rpm. 50 µl of the dense culture was transferred to a new tube containing 1 ml TSB supplemented with spectinomycin and kanamycin. The new culture was then grown at 180 rpm for 2 hrs at 30° C., the cells were centrifuged at 4000 rpm for 15 minutes at 4° C., and the supernatant was replaced by TSB medium supplemented with kan, 10 mM MgCl$_2$, 0.2% arabinose (w/v), and 1 mM IPTG. The media composition supports helper plasmid selection, and recombinase and SceI endonuclease expression to enable insertion. The cells were resuspended and further incubated at 30° C. for 4 hrs at 180 rpm. The cells were centrifuged at 4000 rpm for 15 minutes at 4° C. and newly resuspended in 1 mL TSB MgCl$_2$ 0.2% ara, 1 mM IPTG, and further incubated at 30° C. for 1 h. The dense culture was then plated on TSB plates supplemented with kan (for selection of the DNA insert) and 10% (w/v) sucrose (to counterselect against the donor plasmid) and incubated at 37° C. overnight (to select for loss of the temperature sensitive helper plasmid). A lawn of cells appeared. Streak outs were made on TSB plates supplemented with kan and 10% (w/v) sucrose and incubated at 37° C. overnight.

To screen the resulting colonies for the correct insertion phenotype, single colonies from the streak outs were replica plated onto LB plates supplemented with spec, amp, or kan. Colonies resistant to kan (for presence of the insert), but sensitive for amp and spec (for absence of the donor and helper plasmids) were further analyzed for the insertion.

To confirm that the strain lost the replaced DNA originating from W3110, and contained the DNA insert, colony PCR was performed. Candidate colonies with the correct phenotype were picked and underwent a colony PCR test. Three PCR were executed. i) One PCR uses oligonucleotides 2449/5210 and amplifies the region at the 5' of the inserted DNA only if the recombination happened correctly. ii) One PCR uses oligonucleotides 546/1237 and amplifies the region at the 3' of the inserted DNA only if the recombination happened correctly. iii) One PCR uses oligonucleotides 3454/3455 which give a product only if the target locus has not been modified, meaning unsuccessful recombination. Various clones from the integration showed the right PCR pattern (PCR i and ii positive, PCR iii negative). The resulting strain was designated stLMTB11339.

The following step is the removal of the antibiotic resistances for chloramphenicol (ECA cluster) and kanamycin from the integrated strain. Strain 11339 was transformed with the temperature sensitive pCP20 plasmid expressing the FLP recombinase [1] and plated on LB plates supplemented with ampicillin to select for pCP20. Plates were incubated overnight at 30° C. in order to allow the replication of the plasmid. 5 ml LB cultures were inoculated with streaks from plates and grown overnight at 42° C. to ensure loss of pCP20. Serial dilutions from the overnight cultures were plated on LB plates. 60 single colonies were replicated on LB plates supplemented with ampicillin, kanamycin, chloramphenicol, or without antibiotics. 9 colonies did not grow on plates without antibiotic, no colony grew on kanamycin plates, 15 colonies grew on chloramphenicol (resistance cassette in ECA was not excised), 19 colonies grew on ampicillin plates (pCP20 was retained). A total of 41 colonies showed the correct resistance pattern (growth only on LB plates without antibiotic).

In order to confirm that the loss of resistances is due to the excision of the cassette, and that no genomic material except the resistance cassettes has been lost, two colony PCR were carried out. 1) Kanamycin cassette removal. Using oligonucleotides 3376 and 1265 is expected: i. a 900-bp band if the kanamycin cassette is removed and the DNA bordering the FRT sites is not removed; ii. a 1945-bp band if the kanamycin cassette has not been removed; iii. no PCR product if the DNA region between the FRT3 site and the FRTwt site present in the wca locus has been looped out. 2) Chloramphenicol cassette removal. Using oligonucleotides 3376 and 3495 is expected: i. a 2023-bp band if the chloramphenicol cassette is removed and the DNA bordering the FRT sites is not removed; ii. a 2991-bp band if the chloramphenicol cassette has not been removed.

8 colonies with the right resistance pattern (no ampicillin, chloramphenicol and kanamycin resistances) were tested by colony PCR, and all of them showed the 900-bp band expected if kanamycin resistance cassette is excised and the DNA between the FRT13 and FRTwt sites is intact. Only 4 out of 8 colonies showed the 2023-bp band expected from the chloramphenicol cassette removal, while the other 4 did not give signal in the PCR. As a control, the strain before the resistance removal showed the expected 2991 and 1945-bp bands for the chloramphenicol and kanamycin cassettes, respectively.

The usage of two alternative FRT site pairs (FRT13 for the wca locus replacement, FRTwt for the rfb locus replacement) allowed obtaining a double markerless integration without loss of DNA in these two adjacent loci. Moreover, using two different selection markers allowed the simultaneous excision of the chloramphenicol resistance cassette from the wec ECA cluster and of the kanamycin resistance cassette from the rfb O16 cluster. The resulting strain was named 11340.

Example 5: Preparation of a Strain Devoid of Unwanted Genetic Elements by Usage of Alternative FRT Sites Strain stLMTB10502 is a derivative of *Eschericha coli* W3110 in which the following genes have been deleted: i. waaL, replaced by one FRTwt site; ii. rfb O16 cluster from rfbD to wbbL, replaced by one FRT3 site.

The aim of the genomic manipulation was to delete the wca colanic acid cluster while maintaining intact the short genomic region (2525 bp) between the abovementioned cluster and the rfbD gene (the second gene of the rfb O16 cluster), so that a strain devoid of unwanted sugar cluster can be used as a starting point for further homologous recombinations. The maintenance of the genomic region between the colanic acid and the O16 antigen clusters is fundamental because i, it contains the promoter of the O16 antigen cluster which is exploited for the expression of inserted elements and ii. the strain can be further modified by using donor pDOCs for the O16 antigen cluster replacement as the homologous region are maintained.

The donor pDOC plasmid pLMTB3385 encodes the 5' and 3' homology regions for the replacement of genes from wza to wcaM of the colanic acid cluster. In between them, in the opposite orientation, a kanamycin resistance cassette flanked by two FRT15 sites.

For the replacement, strain 11502 was co-transformed with pTKRED (GenBank: GU327533.1) and the donor plasmid p3385 via electroporation. Because of the temperature sensitive replication phenotype of pTKRED, resulting cells were grown at 30° C. at all times in TSB supplemented with spectinomycin for selection of pTKRED and with kanamycin for selection of p3385. The plasmids were inserted into the acceptor cells to enable the expression of the enzymes encoded on the helper plasmid in the presence of the donor plasmid DNA within the same cell.

Next, the insertion procedure was performed. The freshly transformed strain was grown in TSB medium in the presence of kanamycin and spectinomycin at 30° C. at 5 ml scale overnight at 180 rpm. 50 µl of the dense culture was transferred to a new tube containing 1 ml TSB supplemented with spectinomycin and kanamycin. The new culture was then grown at 180 rpm for 2 hrs at 30° C., the cells were centrifuged at 4000 rpm for 15 minutes at 4° C., and the supernatant was replaced by TSB medium supplemented with kan, 10 mM $MgCl_2$, 0.2% arabinose (w/v), and 1 mM IPTG. The media composition supports helper plasmid selection, and recombinase and SceI endonuclease expression to enable insertion. The cells were resuspended and further incubated at 30° C. for 4 hrs at 180 rpm. The cells were centrifuged at 4000 rpm for 15 minutes at 4° C. and newly resuspended in 1 mL TSB $MgCl_2$ 0.2% ara, 1 mM IPTG, and further incubated at 30° C. for 1 h. The dense culture was then plated on TSB plates supplemented with kan (for selection of the DNA insert) and 10% (w/v) sucrose (to counterselect against the donor plasmid) and incubated at 37° C. overnight (to select for loss of the temperature sensitive helper plasmid). A lawn of cells appeared. Streak outs were made on TSB plates supplemented with kan and 10% (w/v) sucrose and incubated at 37° C. overnight.

To screen the resulting colonies for the correct insertion phenotype, single colonies from the streak outs were replica plated onto LB plates supplemented with spec, amp, or kan. Colonies resistant to kan (for presence of the insert), but sensitive for amp and spec (for absence of the donor and helper plasmids) were further analyzed for the insertion. 11 Of 60 tested clones had the correct pattern, while the remaining showed presistance of ampicillin resistance.

To confirm that the strain lost the replaced DNA originating from W3110, and contained the DNA insert, colony PCR was performed. Candidate colonies with the correct phenotype were picked and underwent a colony PCR test. Three PCR were executed. i) One PCR uses oligonucleotides 3206/4363 and amplifies the region at the 5' of the inserted DNA only if the recombination happened correctly. ii) One PCR uses oligonucleotides 4364/3975 and amplifies the region at the 3' of the inserted DNA only if the recombination happened correctly. iii) One PCR uses oligonucleotides 3872/3957 which give a product only if the target locus has not been modified, meaning unsuccessful recombination. All the clones from the integration showed the right PCR pattern (PCR i and ii positive, PCR iii negative). The resulting strain was designated stLMTB10605.

The following step is the removal of the kanamicin resistance cassette from the integrated strain. Strain 10605 was transformed with the temperature sensitive pCP20 plasmid expressing the FLP recombinase [1] and plated on LB plates supplemented with ampicillin to select for pCP20. Plates were incubated overnight at 30° C. in order to allow the replication of the plasmid. 5 ml LB cultures were inoculated with streaks from plates and grown overnight at 42° C. to ensure loss of pCP20. Serial dilutions from the overnight cultures were plated on LB plates. 10 single colonies were replicated on LB plates supplemented with ampicillin, kanamycin, or without antibiotics. 2 colonies showed the correct resistance patter (growth only on LB plates without antibiotic) and they have been tested in colony PCR.

In order to confirm that the loss of resistances is due to the excision of the cassette, and that no genomic material except the resistance cassettes has been lost, one colony PCR were carried out using oligonucleotides 3206 and 3957, annealing outside the FRT15 sites flanking the kanamycin resistance. A 423-bp band is expected if the kanamycin cassette is removed and the DNA bordering the FRT sites is not removed; a 2862-bp band is expected if the kanamycin cassette has not been removed; no PCR product is expected if the DNA region between the FRT15 site and the FRT3 site present in the rfb locus has been looped out. Both the tested colonies showed the pattern expected from the corret cassette removal.

The usage of two alternative FRT site pairs (FRT15 for the wca locus replacement, FRT3 for the rfb locus replacement) allowed obtaining a double markerless deletion without loss of DNA in these two adjacent loci. This is the first evidence of lack of cross-reactivity between FRT3 and FRT15 sites. The resulting strain was named 10651.

The whole or partial (wzzE to wecG) ECA wca cluster has been later removed from strain 10651 originating strains 10739 and 10740 respectively, which can be used as general starting strains for the development of saccharide-specific bioconjugate production derivatives.

Example 6: Use of Alternative FRT Sites During Strain Development to Allow Integration of Homologous Gene Clusters Strain stLMTB10739 was used as starting strain for the integration of two highly homologous gene clusters.

In the first genetic manipulation, the wca colanic acid cluster was replaced by a heterologous glycan cluster. The donor pDOC plasmid pLMTB2941 encodes the 5' and 3' homology regions for the replacement of the wca cluster. In between them, in the same orientation, a heterologous gene cluster, followed by a chloramphenicol resistance cassette in the opposite orientation flanked by two FRTwt sites.

For the replacement, strain 10739 was co-transformed with pTKRED (GenBank: GU327533.1) and the donor plasmid p2941 via electroporation. Because of the temperature sensitive replication phenotype of pTKRED, resulting cells were grown at 30° C. at all times in TBdev supplemented with spectinomycin for selection of pTKRED and with ampicillin for selection of p2941. The plasmids were inserted into the acceptor cells to enable the expression of the enzymes encoded on the helper plasmid in the presence of the donor plasmid DNA within the same cell.

Next, the insertion procedure was performed. The freshly transformed strain was grown in TBdev medium in the presence of chloramphenicol and spectinomycin at 30° C. at 5 ml scale overnight at 180 rpm. 50 µl of the dense culture was transferred to a new tube containing 2 ml TBdev supplemented with spectinomycin and chloramphenicol. The new culture was then grown at 180 rpm for 3 hrs at 30° C., the cells were centrifuged at 4000 rpm for 5 minutes at 4° C., and the supernatant was replaced by 2 mL TBdev medium supplemented with spc, 0.2% arabinose (w/v), and 1 mM IPTG. The media composition supports helper plasmid selection, and recombinase and SceI endonuclease expression to enable insertion. The cells were resuspended and further incubated at 30° C. for 4 hrs at 180 rpm. The cells were centrifuged at 4000 rpm for 5 minutes at 4° C. and newly resuspended in 2 mL TBdev and further incubated at 37° C. for 1 h. The dense culture was then plated on TBdev plates supplemented with clm (for selection of the DNA insert) and 10% (w/v) sucrose (to counterselect against the donor plasmid) and incubated at 37° C. overnight (to select for loss of the temperature sensitive helper plasmid). A lawn of cells appeared. Streak outs were made on TSB plates supplemented with kan and 10% (w/v) sucrose and incubated at 37° C. overnight.

To screen the resulting colonies for the correct insertion phenotype, 120 single colonies from the streak outs were replica plated onto LB plates supplemented with spec, amp, or clm. Colonies resistant to clm (for presence of the insert), but sensitive for amp and spec (for absence of the donor and helper plasmids) were further analyzed for the insertion. 119 out of 120 clonies were resistant to clm and sensitive to amp and spec.

To confirm that the strain lost the replaced DNA originating from W3110, and contained the DNA insert, colony PCR was performed. Candidate colonies with the correct phenotype were picked and underwent a colony PCR test. Three PCR were executed. i) One PCR uses oligonucleotides 1822/3050 and amplifies the region at the 5' of the inserted DNA only if the recombination happened correctly. ii) One PCR uses oligonucleotides 1366/746 and amplifies the region at the 3' of the inserted DNA only if the recombination happened correctly. iii) One PCR uses oligonucleotides 3967/3969 which amplify part of the inserted genome. 21 out of 21 tested clones from the integration showed the right PCR pattern (PCR i, ii, and iii are positive).

10 clones were tested for functionality. All the tested clones acquired the ability to express the heterologous genes. One performing clone was selected and named stLMTB10867.

As a further step, a second gene cluster with high homology to the first heterologous gene cluster, was inserted in the O16 antigen rfb locus, which is constitutively expressed. If there is a long homology stretch between the wca-integrated cluster and the second glycan gene cluster, it is essential to keep the chloramphenicol resistance pressure during this second homologous recombination procedure. In this way it was possible to select for the wanted recombination event because if the homology stretch would be used as the 5' recombination region, the chloramphenicol resistance cassette would be excised. In this case the donor plasmid is pDOC p3952, encoding the 5' and 3' homology regions for the replacement of the rfb cluster. In between them, in the same orientation, the second gene cluster, followed by a kanamycin resistance cassette in the opposite orientation flanked by two FRT3 sites.

For the replacement, strain 10867 was co-transformed with pTKRED (GenBank: GU327533.1) and the donor plasmid p3952 via electroporation. Because of the temperature sensitive replication phenotype of pTKRED, resulting cells were grown at 30° C. at all times in LB supplemented with spectinomycin for selection of pTKRED and with kanamycin for selection of p3952. The plasmids were inserted into the acceptor cells to enable the expression of the enzymes encoded on the helper plasmid in the presence of the donor plasmid DNA within the same cell.

Next, the insertion procedure was performed. The freshly transformed strain was grown in TBdev medium in the presence of kanamycin and spectinomycin at 28° C. at 5 ml scale overnight at 180 rpm. 50 µl of the dense culture was transferred to a new tube containing 2 ml TBdev supplemented with spectinomycin and chloramphenicol. The new culture was then grown at 180 rpm for 3 hrs at 30° C., the cells were centrifuged at 4000 rpm for 5 minutes at 4° C., and the supernatant was replaced by 2 mL TBdev medium supplemented with spc, 0.2% arabinose (w/v), and 1 mM IPTG. The media composition supports helper plasmid selection, and recombinase and SceI endonuclease expression to enable insertion. The cells were resuspended and further incubated at 30° C. for 4 hrs at 180 rpm. 50 uL of the culture was used to inoculate 2 mL TBdev with 0.2% arabinose (w/v) and 1 mM IPTG, which were grown over night at 30° C. The following day the culture were put 1 hour at 37° C. and then plated on TBdev plates supplemented with kan (for selection of the DNA insert), clm (for selection of the wanted recombination event), and 10% (w/v) sucrose (to counterselect against the donor plasmid) and incubated at 37° C. overnight (to select for loss of the temperature sensitive helper plasmid). A lawn of cells appeared. Streak outs were made on TBdev plates supplemented with clm, kan, and 10% (w/v) sucrose and incubated at 37° C. overnight.

To screen the resulting colonies for the correct insertion phenotype, 60 single colonies from the streak outs were replica plated onto LB plates supplemented with spec, amp, or clm+kan. Colonies resistant to clm and kan (for presence of the insert and with correct recombination pattern), but sensitive for amp and spec (for absence of the donor and helper plasmids) were further analyzed for the insertion. 55 out of 60 clonies displayed the wanted resistance pattern.

Candidate colonies with the correct phenotype were picked and underwent a colony PCR test. Two PCR were executed. i) One PCR uses oligonucleotides 3204/3940 and amplifies the region at the 5' of the inserted DNA only if the recombination happened correctly, and the genetic material between the wca and rfb loci did not get lost. ii) One PCR uses oligonucleotides 548/1237 and amplifies the region at the 3' of the inserted DNA only if the recombination happened correctly. iii) One PCR uses oligonucleotides 3967/3969 which amplify part of the inserted genome. 30 colonies were screened first for PCR i. 3 positive colonies were found. PCRs ii and iii. were carried out only on these colonies and resulted to be positive for all of them.

The three clones were tested for functionality (enzyme expression). All the tested clones acquired the ability to express the expected enzymes, specifically from the rfb cluster (see below for explanation). One performing clone was selected and named stLMTB10883.

The following step is the removal of the antibiotic resistances for chloramphenicol (colanic acid wca cluster) and kanamycin (above-mentioned integration in O16 cluster) from the integrated strain. Strain 10883 was transformed with the temperature sensitive pCP20 plasmid expressing the FLP recombinase [1] and plated on LB plates supplemented with ampicillin to select for pCP20. Plates were incubated overnight at 30° C. in order to allow the replication of the plasmid. 5 ml LB cultures were inoculated with streaks from plates and grown overnight at 42° C. to ensure loss of pCP20. Serial dilutions from the overnight cultures were plated on LB plates. 20 single colonies were replicated on LB plates supplemented with ampicillin, kanamycin, chloramphenicol, or without antibiotics. All the colonies showed the correct resistance patter (growth only on LB plates without antibiotic).

In order to confirm that the loss of resistances is due to the excision of the cassette, and that no genomic material except the resistance cassettes has been lost, two colony PCR were carried out. i. Kanamycin cassette removal using oligonucleotides 3966 and 1237 which bind outside the FRT3 sites; ii. chloramphenicol cassette removal using oligonucleotides 3929 and 1231 which bind outside the FRTwt sites. The three screened colonies had pattern expected from correct removal of the kanamycin cassette. 2 of them were tested for the chloramophenicol PCR and also resulted in expected pattern. On of the two confirmend clones resulting from this kanamycin/chloramphenicol removal was named stLMTB10900.

The usage of two alternative FRT site pairs (FRT13 for the rfb locus replacement, FRTwt for the wca locus replacement) allowed obtaining a double markerless integration without loss of DNA in these two adjacent loci. In this particular case the simultaneous removal was essential as the persistence of the chloramphenicol cassette during the insertion of the second copy of the cluster and the kanamycin resistance cassette was strictly necessary for the selection for the correct recombination event.

27_0048 Strains 10739, 10867, 10883, and 10900 were tested and compared for functionality by obtaining competent cells and transforming them with different sets of plasmid. 5 mL TBdev 10 mM $MgCl_2$ supplemented with proper antibiotics were inoculated with 10 uL of the recovery suspension and grown over night at 37° C. 50 mL TBdev 10 mM $MgCl_2$ and antibiotics main cultures were inoculated to $OD_{600}$ 0.1 and shaked at 37° C. Induction was carried out at $OD_{600}$ 0.8 to 1 with 1 mM IPTG and 0.1% arabinose where necessary. Cultures were grown over night at 37° C. The volume corresponding to 2 OD was harvested, resuspended into 100 uL of Lämmli buffer, heated 10 minutes at 95° C. Proteinase K was added and incubated at 55° C. for one hour, followed by 10 minutes at 70° C. for inactivation. Samples were thoroughly vortexed and spun down. The volume corresponding to 0.4 OD was loaded on an SDS-page gel. After the run, transfer onto a membrane and following Western Blot the measure the function of the expressed enzymes. The wca-encoded cluster relies on the expression of rcsA for its own expression, while the rfb-encoded cluster is active but biosynthesis requires wchA. The plasmid combinations used have been selected in order to understand if both clusters are active. It is possible to observe that both the integrated clusters are functional: presence of wchA in strain 10883 and 10900 results in the production of antiserum-reactive species, while addition of rcsA activates the wca-integrated cluster resulting in antiserum-reactive species.

Example 7: Useful Sequences for Carrying Out the Deletion of Insert DNA

```
FRTwt
                                            SEQ ID NO: 1
5'-GAAGTTCCTATTCCGAAGTTCCTATTCTCTAGAAAGTATAGGAACT
TC-3'

FRT3
                                            SEQ ID NO: 2
5'-GAAGTTCCTATTCCGAAGTTCCTATTCTTCAAATAGTATAGGAACT
TC-3'

FRT10
                                            SEQ ID NO: 3
5'-GAAGTTCCTATTCCGAAGTTCCTATTCACTAGAATGTATAGGAACT
TC-3'
```

-continued

FRT13
SEQ ID NO: 4
5'-GAAGTTCCTATTCCGAAGTTCCTATTCTCATATAAGTATAGGAACT
TC-3'

FRT14
SEQ ID NO: 5
5'-GAAGTTCCTATTCCGAAGTTCCTATTCTATCAGAAGTATAGGAACT
TC-3'

FRT15
SEQ ID NO: 6
5'-GAAGTTCCTATTCCGAAGTTCCTATTCTTATAGGAGTATAGGAACT
TC-3'

FRT5
SEQ ID NO: 7
5'-GAAGTTCCTATTCCGAAGTTCCTATTCACTAGAATGTATAGGAACT
TC-3'

FRT11
SEQ ID NO: 8
5'-GAAGTTCCTATTCCGAAGTTCCTATTCTGAACTAAGTATAGGAACT
TC-3'

FRT12
SEQ ID NO: 9
5'-GAAGTTCCTATTCCGAAGTTCCTATTCTTTCTGAAGTATAGGAACT
TC-3'

FRT16
SEQ ID NO: 10
5'-GAAGTTCCTATTCCGAAGTTCCTATTCTCCGGGCAGTATAGGAACT
TC-3'

FLP recombinase
SEQ ID NO: 11
MPQFDILCKTPPKVLVRQFVERFERPSGEKIALCAAELTYLCWMITHNG
TAIKRATFMSYNTIISNSLSFDIVNKSLQFKYKTQKATILEASLKKLIP
AWEFTIIPYYGQKHQSDITDIVSSLQLQFESSEEADKGNSHSKKMLKAL
LSEGESIWEITEKILNSFEYTSRFTKTKTLYQFLFLATFINCGRFSDIK
NVDPKSFKLVQNKYLGVIIQCLVTETKTSVSRHIYFFSARGRTDPLVYL
DEFLRNSEPVLKRVNRTGNSSSNKQEYQLLKDNLVRSYNKALKKNAPYS
IFAIKNGPKSHIGRHLMTSFLSMKGLTELTNVVGNWSDKRASAVARTTY
THQITAIPDHYFALVSRYYAYDPISKEMIALKDETNPIEEWQHIEQLKG
SAEGSIRYPAWNGIISQEVLDYLSSYINRRI FLP recombinase
SEQ ID NO: 12
ATGCCACAATTTGATATATTATGTAAAACACCACCTAAGGTGCTTGTTC
GTCAGTTTGTGGAAAGGTTTGAAAGACCTTCAGGTGAGAAAATAGCATT
ATGTGCTGCTGAACTAACCTATTTATGTTGGATGATTACACATAACGGA
ACAGCAATCAAGAGAGCCACATTCATGAGCTATAATACTATCATAAGCA
ATTCGCTGAGTTTCGATATTGTCAATAAATCACTCCAGTTTAAATACAA
GACGCAAAAAGCAACAATTCTGGAAGCCTCATTAAAGAAATTGATTCCT
GCTTGGGAATTTACAATTATTCCTTACTATGGACAAAAACATCAATCTG
ATATCACTGATATTGTAAGTAGTTTGCAATTACAGTTCGAATCATCGGA AGAAGCAGATAAGGGAAATAGCCACAGTAAAAAAATGCTTAAAGCACTT
CTAAGTGAGGGTGAAAGCATCTGGGAGATCACTGAGAAAATACTAAATT
CGTTTGAGTATACTTCGAGATTTACAAAAACAAAAACTTTATACCAATT
CCTCTTCCTAGCTACTTTCATCAATTGTGGAAGATTCAGCGATATTAAG
AACGTTGATCCGAAATCATTTAAATTAGTCCAAAATAAGTATCTGGGAG
TAATAATCCAGTGTTTAGTGACAGAGACAAAGACAAGCGTTAGTAGGCA
CATATACTTCTTTAGCGCAAGGGGTAGGATCGATCCACTTGTATATTTG
GATGAATTTTTGAGGAATTCTGAACCAGTCCTAAAACGAGTAAATAGGA
CCGGCAATTCTTCAAGCAATAAACAGGAATACCAATTATTAAAAGATAA
CTTAGTCAGATCGTACAATAAAGCTTTGAAGAAAAATGCGCCTTATTCA
ATCTTTGCTATAAAAAATGGCCCAAAATCTCACATTGGAAGACATTTGA
TGACCTCATTTCTTTCAATGAAGGGCCTAACGGAGTTGACTAATGTTGT
GGGAAATTGGAGCGATAAGCGTGCTTCTGCCGTGGCCAGGACAACGTAT
ACTCATCAGATAACAGCAATACCTGATCACTACTTCGCACTAGTTTCTC
GGTACTATGCATATGATCCAATATCAAAGGAAATGATAGCATTGAAGGA
TGAGACTAATCCAATTGAGGAGTGGCAGCATATAGAACAGCTAAAGGGT
AGTGCTGAAGGAAGCATACGATACCCCGCATGGAATGGGATAATATCAC
AGGAGGTACTAGACTACCTTTCATCCTACATAAATAGACGCATA pCP20 containing FLP gene
SEQ ID NO: 13
GAGACACAACGTGGCTTTGTTGAATAAATCGAACTTTTGCTGAGTTGAA
GGATCAGATCACGCATCTTCCCGACAACGCAGACCGTTCCGTGGCAAAG
CAAAAGTTCAAAATCACCAACTGGTCCACCTACAACAAAGCTCTCATCA
ACCGTGGCTCCCTCACTTTCTGGCTGGATGATGGGGCGATTCAGGCCTG
GTATGAGTCAGCAACACCTTCTTCACGAGGCAGACCTCAGCGCCACAGG
TGCGGTTGCTGGCGCTAACCGTTTTTATCAGGCTCTGGGAGGCAGAATA
AATGATCATATCGTCAATTATTACCTCCACGGGGAGAGCCTGAGCAAAC
TGGCCTCAGGCATTTGAGAAGCACACGGTCACACTGCTTCCGGTAGTCA
ATAAACCGGTAAACCAGCAATAGACATAAGCGGCTATTTAACGACCCTG
CCCTGAACCGACGACCGGGTCGAATTTGCTTTCGAATTTCTGCCATTCA
TCCGCTTATTATCACTTATTCAGGCGTAGCAACCAGGCGTTTAAGGGCA
CCAATAACTGCCTTAAAAAAATTACGCCCCGCCCTGCCACTCATCGCAG
TACTGTTGTAATTCATTAAGCATTCTGCCGACATGGAAGCCATCACAAA
CGGCATGATGAACCTGAATCGCCAGCGGCATCAGCACCTTGTCGCCTTG
CGTATAATATTTGCCCATGGTGAAAACGGGGGCGAAGAAGTTGTCCATA
TTGGCCACGTTTAAATCAAAACTGGTGAAACTCACCCAGGGATTGGCTG
AGACGAAAACATATTCTCAATAAACCCTTTAGGGAAATAGGCCAGGTT
TTCACCGTAACACGCCACATCTTGCGAATATATGTGTAGAAACTGCCGG
AAATCGTCGTGGTATTCACTCCAGAGCGATGAAAACGTTTCAGTTTGCT
CATGGAAAACGGTGTAACAAGGGTGAACACTATCCCATATCACCAGCTC
ACCGTCTTTCATTGCCATACGGAATTCCGGATGAGCATTCATCAGGCGG
GCAAGAATGTGAATAAAGGCCGGATAAAACTTGTGCTTATTTTTCTTTA CGGTCTTTAAAAAGGCCGTAATATCCAGCTGAACGGTCTGGTTATAGGT
ACATTGAGCAACTGACTGAAATGCCTCAAAATGTTCTTTACGATGCCAT
TGGGATATATCAACGGTGGTATATCCAGTGATTTTTTCTCCATTTTAG
CTTCCTTAGCTCCTGAAAATCTCGATAACTCAAAAAATACGCCCGGTAG
TGATCTTATTTCATTATGGTGAAAGTTGGAACCTCTTACGTGCCGATCA
ACGTCTCATTTTCGCCAAAAGTTGGCCCAGGGCTTCCCGGTATCAACAG
GGACACCAGGATTTATTTATTCTGCGAAGTGATCTTCCGTCACAGGTAT
TTATTCGGCGCAAAGTGCGTCGGGTGATGCTGCCAACTTACTGATTTAG
TGTATGATGGTGTTTTTGAGGTGCTCCAGTGGCTTCTGTTTCTATCAGC
TGTCCCTCCTGTTCAGCTACTGACGGGGTGGTGCGTAACGGCAAAAGCA
CCGCCGGACATCAGCGCTTGTTTCGGCGTGGGTATGGTGGCAGGCCCCG
TGGCCGGGGGACTGTTGGGCGCCTGTAGTGCCATTTACCCCCATTCACT
GCCAGAGCCGTGAGCGCAGCGAACTGAATGTCACGAAAAAGACAGCGAC
TCAGGTGCCTGATGGTCGGAGACAAAAGGAATATTCAGCGATTTGCCCG
AGCTTGCGAGGGTGCTACTTAAGCCTTTAGGGTTTTAAGGTCTGTTTTG
TAGAGGAGCAAACAGCGTTTGCGACATCCTTTTGTAATACTGCGGAACT
GACTAAAGTAGTGAGTTATACACAGGGCTGGGATCTATTCTTTTTATCT
TTTTTTATTCTTTCTTTATTCTATAAATTATAACCACTTGAATATAAAC
AAAAAAAACACACAAAGGTCTAGCGGAATTTACAGAGGGTCTAGCAGAA
TTTACAAGTTTTCCAGCAAAGGTCTAGCAGAATTTACAGATACCCACAA
CTCAAAGGAAAAGGACTAGTAATTATCATTGACTAGCCCATCTCAATTG
GTATAGTGATTAAAATCACCTAGACCAATTGAGATGTATGTCTGAATTA
GTTGTTTTCAAAGCAAATGAACTAGCGATTAGTCGCTATGACTTAACGG
AGCATGAAACCAAGCTAATTTTATGCTGTGTGGCACTACTCAACCCCAC
GATTGAAAACCCTACAAGGAAAGAACGGACGGTATCGTTCACTTATAAC
CAATACGTTCAGATGATGAACATCAGTAGGGAAAATGCTTATGGTGTAT
TAGCTAAAGCAACCAGAGAGCTGATGACGAGAACTGTGGAAATCAGGAA
TCCTTTGGTTAAAGGCTTTGAGATTTTCCAGTGGACAAACTATGCCAAG
TTCTCAAGCGAAAAATTAGAATTAGTTTTTAGTGAAGAGATATTGCCTT
ATCTTTTCCAGTTAAAAAAATTCATAAAATATAATCTGGAACATGTTAA
GTCTTTTGAAAACAAATACTCTATGAGGATTTATGAGTGGTTATTAAAA
GAACTAACACAAAAGAAAACTCACAAGGCAAATATAGAGATTAGCCTTG
ATGAATTTAAGTTCATGTTAATGCTTGAAAATAACTACCATGAGTTTAA
AAGGCTTAACCAATGGGTTTTGAAACCAATAAGTAAAGATTTAAACACT
TACAGCAATATGAAATTGGTGGTTGATAAGCGAGGCCGCCCGACTGATA
CGTTGATTTTCCAAGTTGAACTAGATAGACAAATGGATCTCGTAACCGA
ACTTGAGAACAACCAGATAAAAATGAATGGTGACAAAATACCAACAACC
ATTACATCAGATTCCTACCTACATAACGGACTAAGAAAAACACTACACG
ATGCTTTAACTGCAAAAATTCAGCTCACCAGTTTTGAGGCAAATTTTT
GAGTGACATGCAAAGTAAGTATGATCTCAATGGTTCGTTCTCATGGCTC ACGCAAAAACAACGAACCACACTAGAGAACATACTGGCTAAATACGGAA
GGATCTGAGGTTCTTATGGCTCTTGTATCTATCAGTGAAGCATCAAGAC
TAACAAACAAAAGTAGAACAACTGTTCACCGTTACATATCAAAGGGAAA
ACTGTCCATATGCACAGATGAAAACGGTGTAAAAAAGATAGATACATCA
GAGCTTTTACGAGTTTTTGGTGCATTTAAAGCTGTTCACCATGAACAGA
TCGACAATGTAACAGATGAACAGCATGTAACACCTAATAGAACAGGTGA
AACCAGTAAAACAAAGCAACTAGAACATGAAATTGAACACCTGAGACAA
CTTGTTACAGCTCAACAGTCACACATAGACAGCCTGAAACAGGCGATGC
TGCTTATCGAATCAAAGCTGCCGACAACACGGGAGCCAGTGACGCCTCC
CGTGGGGAAAAAATCATGGCAATTCTGGAAGAAATAGCGCCTGTTTCGT
TTCAGGCAGGTTATCAGGGAGTGTCAGCGTCCTGCGGTTCTCCGGGGCG
TTCGGGTCATGCAGCCCGTAATGGTGATTTACCAGCGTCTGCCAGGCAT
CAATTCTAGGCCTGTCTGCGCGGTCGTAGTACGGCTGGAGGCGTTTTCC
GGTCTGTAGCTCCATGTTCGGAATGACAAAATTCAGCTCAAGCCGTCCC
TTGTCCTGGTGCTCCACCCACAGGATGCTGTACTGATTTTTTTCGAGAC
CGGGCATCAGTACACGCTCAAAGCTCGCCATCACTTTTTCACGTCCTCC
CGGCGGCAGCTCCTTCTCCGCGAACGACAGAACACCGGACGTGTATTTC
TTCGCAAATGGCGTGGCATCGATGAGTTCCCGGACTTCTTCCGGATTAC
CCTGAAGCACCGTTGCGCCTTCGCGGTTACGCTCCCTCCCCAGCAGGTA
ATCAACCGGACCACTGCCACCACCTTTTCCCCTGGCATGAAATTTAACTA
TCATCCCGCGCCCCTGTTCCCTGACAGCCAGACGCAGCCGGCGCAGCTC
ATCCCCGATGGCCATCAGTGCGGCCACCACCTGAACCCGGTCACCGGAAG
ACCACTGCCCGCTGTTCACCTTACGGGCTGTCTGATTCAGGTTATTTCCG
ATGGCGGCCAGCTGACGCAGTAACGGCGGTGCCAGTGTCGGCAGTTTTCC
GGAACGGGCAACCGGCTCCCCAGGCAGACCCGCCGCATCCATACCGCCA
GTTGTTTACCCTCACAGCGTTCAAGTAACCGGGCATGTTCATCATCAGTA
ACCCGTATTGTGAGCATCCTCTCGCGTTTCATCGGTATCATTACCCCATG
AACAGAAATCCCCCTTACACGGAGGCATCAGTGACTAAACGGGGTCTGAC
GCTCAGTGGAACGAAAACTCACGTTAAGGGATTTTGGTCATGAGATTATC
AAAAAGGATCTTCACCTAGATCCTTTTAAATTAAAAATGAAGTTTTAAAT
CAATCTAAAGTATATATGAGTAAACTTGGTCTGACAGTTACCAATGCTTA
ATCAGTGAGGCACCTATCTCAGCGATCTGTCTATTTCGTTCATCCATAGT
TGCCTGACTCCCCGTCGTGTAGATAACTACGATACGGGAGGGCTTACCAT
CTGGCCCCAGTGCTGCAATGATACCGCGAGACCCACGCTCACCGGCTCCA
GATTTATCAGCAATAAACCAGCCAGCCGGAAGGGCCGAGCGCAGAAGTGG
TCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATT
GCTGCAGGCATCGTGGTGTCACGCTCGTCGTTTGGTATGGCTTCATTCAG
CTCCGGTTCCCAACGATCAAGGCGAGTTACATGATCCCCCATGTTGTGCA
AAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTAC -continued

TGTCATGCCATCCGTAAGATGCTTTTCTGTGACTGGTGAGTACTCAACCA

AGTCATTCTGAGAATAGTGTATGCGGCGACCGAGTTGCTCTTGCCCGGCG

TCAACACGGGATAATACCGCGCCACATAGCAGAACTTTAAAAGTGCTCAT

CATTGGAAAACGTTCTTCGGGGCGAAAACTCTCAAGGATCTTACCGCTGT

TGAGATCCAGTTCGATGTAACCCACTCGTGCACCCAACTGATCTTCAGCA

TCTTTTACTTTCACCAGCGTTTCTGGGTGAGCAAAAACAGGAAGGCAAAA

TGCCGCAAAAAAGGGAATAAGGGCGACACGGAAATGTTGAATACTCATAC

TCTTCCTTTTTCAATATTATTGAAGCATTTATCAGGGTTATTGTCTCATG

AGCGGATACATATTTGAATGTATTTAGAAAAATAAACAAATAGGGGTTCC

GCGCACATTTCCCCGAAAAGTGCCACCTGACGTCTAAGAAACCATTATTA

TCATGACATTAACCTATAAAAATAGGCGTATCACGAGGCCCTTTCGTCTT

CAAGAATTTTATAAACCGTGGAGCGGGCAATACTGAGCTGATGAGCAATT

TCCGTTGCACCAGTGCCCTTCTGATGAAGCGTCAGCACGACGTTCCTGTC

CACGGTACGCCTGCGGCCAAATTTGATTCCTTTCAGCTTTGCTTCCTGTC

GGCCCTCATTCGTGCGCTCTAGGATCCTCTACGCCGGACGCATCGTGGCC

GGCATCACCGGCGCTGAGGTCTGCCTCGTGAAGAAGGTGTTGCTGACTCA

TACCAGGCCTGAATCGCCCCATCATCCAGCCAGAAAGTGAGGGAGCCACG

GTTGATGAGAGCTTTGTTGTAGGTGGACCAGTTGGTGATTTTGAACTTTT

GCTTTGCCACGGAACGGTCTGCGTTGTCGGGAAGATGCGTGATCTGATCC

TTCAACTCAGCAAAAGTTCGATTTATTCAACAAAGCCGCCGTCCCGTCAA

GTCAGCGTAATGCTCTGCCAGTGTTACAACCAATTAACCAATTCTGATTA

GAAAACTCATCGAGCATCAAATGAAACTGCAATTTATTCATATCAGGAT

TATCAATACCATATTTTTGAAAAAGCCGTTTCTGTAATGAAGGAGAAAAC

TCACCGAGGCAGTTCCATAGGATGGCAAGATCCTGGTATCGGTCTGCGAT

TCCGACTCGTCCAACATCAATACAACCTATTAATTTCCCCTCGTCAAAAA

TAAGGTTATCAAGTGAGAAATCACCATGAGTGACGACTGAATCCGGTGAG

AATGGCAGAATAGGAACTTCGGAATAGGAACTTCAAAGCGTTTCCGAAAA

CGAGCGCTTCCGAAAATGCAACGCGAGCTGCGCACATACAGCTCACTGTT

CACGTCGCACCTATATCTGCGTGTTGCCTGTATATATATACATGAGAA

GAACGGCATAGTGCGTGTTTATGCTTAAATGCGTACTTATATGCGTCTAT

TTATGTAGGATGAAAGGTAGTCTAGTACCTCCTGTGATATTATCCCATTC

CATGCGGGGTATCGTATGCTTCCTTCAGCACTACCCTTTAGCTGTTCTAT

ATGCTGCCACTCCTCAATTGGATTAGTCTCATCCTTCAATGCTATCATTT

CCTTTGATATTGGATCATATGCATAGTACCGAGAAACTAGTGCGAAGTAG

TGATCAGGTATTGCTGTTATCTGATGAGTATACGTTGTCCTGGCCACGGC

AGAAGCACGCTTATCGCTCCAATTTCCCACAACATTAGTCAACTCCGTTA

GGCCCTTCATTGAAAGAAATGAGGTCATCAAATGTCTTCCAATGTGAGAT

TTTGGGCCATTTTTTATAGCAAAGATTGAATAAGGCGCATTTTTCTTCAA

AGCTTTATTGTACGATCTGACTAAGTTATCTTTTAATAATTGGTATTCCT

GTTTATTGCTTGAAGAATTGCCGGTCCTATTTACTCGTTTTAGGACTGGT

TCAGAATTCCTCAAAAATTCATCCAAATATACAAGTGGATCGATCCTACC

CCTTGCGCTAAAGAAGTATATGTGCCTACTAACGCTTGTCTTTGTCTCTG

TCACTAAACACTGGATTATTACTCCCAGATACTTATTTTGGACTAATTTA

AATGATTTCGGATCAACGTTCTTAATATCGCTGAATCTTCCACAATTGAT

GAAAGTAGCTAGGAAGAGGAATTGGTATAAAGTTTTTGTTTTTGTAAATC

TCGAAGTATACTCAAACGAATTTAGTATTTTCTCAGTGATCTCCCAGATG

CTTTCACCCTCACTTAGAAGTGCTTTAAGCATTTTTTTACTGTGGCTATT

TCCCTTATCTGCTTCTTCCGATGATTCGAACTGTAATTGCAAACTACTTA

CAATATCAGTGATATCAGATTGATGTTTTTGTCCATAGTAAGGAATAATT

GTAAATTCCCAAGCAGGAATCAATTTCTTTAATGAGGCTTCCAGAATTGT

TGCTTTTTGCGTCTTGTATTTAAACTGGAGTGATTTATTGACAATATCGA

AACTCAGCGAATTGCTTATGATAGTATTATAGCTCATGAATGTGGCTCTC

TTGATTGCTGTTCCGTTATGTGTAATCATCCAACATAAATAGGTTAGTTC

AGCAGCACATAATGCTATTTTCTCACCTGAAGGTCTTTCAAACCTTTCCA

CAAACTGACGAACAAGCACCTAGGTGGTGTTTTACATAATATATCAAAT

TGTGGCATACAACCTCCTTAGTACATGCAACCATTATCACCGCCAGAGGT

AAAATAGTCAACACGCACGGTGTTAGATATTTATCCCTTGCGGTGATAGA

TTTAACGTATGAGCACAAAAAGAAACCATTAACACAAGAGCAGCTTGAG

GACGCACGTCGCCTTAAAGCAATTTATGAAAAAAGAAAAATGAACTTGG

CTTATCCCAGGAATCTGTCGCAGACAAGATGGGGATGGGGCAGTCAGGCG

TTGGTGCTTTATTTAATGGCATCAATGCATTAAATGCTTATAACGCCGCA

TTGCTTACAAAAATTCTCAAAGTTAGCGTTGAAGAATTTAGCCCTTCAAT

CGCCAGAGAAATCTACGAGATGTATGAAGCGGTTAGTATGCAGCCGTCAC

TTAGAAGTGAGTATGAGTACCCTGTTTTTTCTCATGTTCAGGCAGGGATG

TTCTCACCTAAGCTTAGAACCTTTACCAAAGGTGATGCGGAGAGATGGGT

AAGCACAACCAAAAAGCCAGTGATTCTGCATTCTGGCTTGAGGTTGAAG

GTAATTCCATGACCGCACCAACAGGCTCCAAGCCAAGCTTTCCTGACGGA

ATGTTAATTCTCGTTGACCCTGAGCAGGCTGTTGAGCCAGGTGATTTCTG

CATAGCCAGACTTGGGGGTGATGAGTTTACCTTCAAGAAACTGATCAGGG

ATAGCGGTCAGGTGTTTTACAACCACTAAACCCACAGTACCCAATGATC

CCATGCAATGAGAGTTGTTCCGTTGTGGGGAAAGTTATCGCTAGTCAGTG

GCCTGAAGAGACGTTTGGCTGATCGGCAAGGTGTTCTGGTCGGCGCATAG

CTGATAACAATTGAGCAAGAATCTGCATTTCTTTCCAGACTTGTTCAACA

GGCCAGCCATTACGCTCGTCATCAAAATCACTCGCATCAACCAAACCGTT

ATTCATTCGTGATTGCGCCTGAGCGAGACGAAATACGCGATCGCTGTTAA

AAGGACAATTACAAACAGGAATCGAATGCAACCGGCGCAGGAACACTGCC

AGCGCATCAACAATATTTTCACCTGAATCAGGATATTCTTCTAATACCTG

GAATGCTGTTTTCCCGGGGATCGCAGTGGTGAGTAACCATGCATCATCAG

GAGTACGGATAAAATGCTTGATGGTCGGAAGAGGCATAAATTCCGTCAGC

CAGTTTAGTCTGACCATCTCATCTGTAACATCATTGGCAACGCTACCTTT

GCCATGTTTCAGAAACAACTCTGGCGCATCGGGCTTCCCATACAATCGAT

AGATTGTCGCACCTGATTGCCCGACATTATCGCGAGCCCATTTATACCCA

TATAAATCAGCATCCATGTTGGAATTTAATCGCGGCCTCGAGCAAGACGT

TTCCCGTTGAATATGGCTCATAACACCCCTTGTATTACTGTTTATGTAAG

CAGACAGTTTTATTGTTCATGATGATATATTTTTATCTTGTGCAATGTAA

CATCAGAGATTTT

---

What is claimed is:

1. A host cell comprising a host cell genome polynucleotide containing a first recombinantly engineered region, a second recombinantly engineered region, a first recombination site scar and a second recombination site scar,
wherein the first recombination site scar comprise a nucleic acid sequence of the SEQ ID NO:1, 2, 3, 4, 5, 6, 7, 8, 9 or 10, and is adjacent to the first recombinantly engineered region in which part of the genomic polynucleotide has been engineered by the addition, deletion or replacement of a nucleic acid sequence, and
the second recombination site scar is adjacent to the second recombinantly engineered region in which part of the genomic polynucleotide has been engineered by the addition, deletion or replacement of nucleic acid sequence;
wherein the first recombinantly engineered region comprises deletion of a waaL gene and the second recombinantly engineered region comprises deletion of at least part of a wca colonic acid cluster and/or deletion of at least part of an rfb cluster,
wherein the first and second recombination site scars have different polynucleotide sequences and the sequence of the second scar is less than 98% identical to SEQ ID NO:1, 2, 3, 4, 5, 6, 7, 8, 9 or 10, and wherein the first and second recombination sites are 30-50 base pairs in length and where the first or second recombination site is a FRT site said FRT site is 48 base pairs in length.

2. The host cell of claim 1, wherein the first and second recombination sites scars are formed from first and second recombination sites for an FLP recombinase.

3. The host cell of claim 2, wherein the first recombination site has the nucleic acid sequence of SEQ ID NO:1.

4. The host cell of claim 1, wherein the first and second recombination sites scars are separated by less than 100, 75, 50, 25, 10 or 5 kbases.

* * * * *